United States Patent
Bruzenak et al.

(10) Patent No.: US 9,739,726 B2
(45) Date of Patent: Aug. 22, 2017

(54) FRONT-LOADING SAMPLE PREPARATION APPARATUS

(71) Applicant: FLSmidth A/S, Valby (DK)

(72) Inventors: Lukas Bruzenak, Brno (CZ); Vladimir Meleg, Račice-Pístovice (CZ)

(73) Assignee: FLSMIDTH A/S, Valby (DK)

(*) Notice: Subject to any disclaimer, the term of this patent is extended or adjusted under 35 U.S.C. 154(b) by 32 days.

(21) Appl. No.: 15/023,633

(22) PCT Filed: Sep. 18, 2014

(86) PCT No.: PCT/EP2014/069917
§ 371 (c)(1),
(2) Date: Mar. 21, 2016

(87) PCT Pub. No.: WO2015/040123
PCT Pub. Date: Mar. 26, 2015

(65) Prior Publication Data
US 2016/0290938 A1 Oct. 6, 2016

Related U.S. Application Data

(60) Provisional application No. 61/880,094, filed on Sep. 19, 2013.

(51) Int. Cl.
*G01N 23/20* (2006.01)
*G01N 1/28* (2006.01)

(52) U.S. Cl.
CPC ........ *G01N 23/2005* (2013.01); *G01N 1/286* (2013.01); *G01N 2223/056* (2013.01); *G01N 2223/307* (2013.01); *G01N 2223/312* (2013.01); *G01N 2223/616* (2013.01)

(58) Field of Classification Search
CPC .............. G01N 23/2005; G01N 1/286; G01N 2223/312; G01N 2223/307; G01N 2223/616; G01N 2223/056
USPC ................................ 73/863–864; 374/68–69
See application file for complete search history.

(56) References Cited

FOREIGN PATENT DOCUMENTS

| EP | 2141479 A2 | 1/2010 |
|---|---|---|
| JP | 2002148163 A | 5/2002 |

OTHER PUBLICATIONS

English machine translation for JP 2002148163.*
(Continued)

*Primary Examiner* — Daniel S Larkin
*Assistant Examiner* — Anthony W Megna Fuentes
(74) *Attorney, Agent, or Firm* — Jeffrey A. Sharp

(57) ABSTRACT

Disclosed, is a sample preparation apparatus which is configured to prepare a material sample suitable for X-ray diffraction. The apparatus comprises a dished sample holder bottom configured to fit within an annular sample holder. The dished sample holder bottom has a concave dished surface which is adapted to distribute sample material under pressing forces. A method of preparing a material sample suitable for X-ray diffraction is also disclosed. The method comprises dosing a dished sample holder bottom which is configured to fit within an annular sample holder with sample material, wherein the dished sample holder bottom preferably has a concave dished surface which is adapted to distribute sample material under pressing forces.

12 Claims, 19 Drawing Sheets

(56) References Cited

OTHER PUBLICATIONS

IMP Innovative Solutions, Herzog-XRD-automation, Herzog-XRD-automation, Aug. 1, 2011, Entire brochure, Aug. 2011http://www.impautomation.com/getfile.p hp?file=images/XRD Automation.pdf.

International Search Report and Written Opinion dated Apr. 17, 2015, 15 pages.

* cited by examiner

FRONT-LOADING SAMPLE PREPARATION APPARATUS

CROSS-REFERENCE OF RELATED APPLICATIONS

This application is an international application which claims the benefit of U.S. Provisional Patent Application No. 61/880,094 filed on 19 Sep. 2013.

BACKGROUND OF THE INVENTION

This invention relates to sample preparation equipment and methods, and more particularly to diffractometry sample preparation systems, and most particularly to a front-loading soft press system for preparing X-ray diffraction (XRD) samples in minerals processing industries.

X-ray powder diffraction (XRD) is a rapid analytical technique primarily used for phase identification of a crystalline material and it can provide information on unit cell dimensions. The technique generally involves the steps of providing sample material, finely grinding the sample material, homogenizing the finely-ground sample material, and determining the average bulk composition of the homogenized sample.

The current standard sample preparation technique is known as "back-loading", wherein sample material is first poured into sample holder having a bottom surface, the sample material is pressed into the sample holder forming a sample material measuring surface adjacent the bottom surface of the sample holder, removing the sample holder, and measuring the sample material at a measuring surface formed by the bottom surface of the sample holder. The bottom surface of the sample holder is textured so as to impart a sample material measuring surface which has defined, repeatable roughness characteristics. Since the measuring surface of the pressed sample is not necessarily affected by direct pressure imparted by a pressing component or by physical surface interactions with pressing components during pressing of the sample material, the phenominon well-known as "preferred orientation" is reduced at the measuring surface of the prepared sample. FIG. 2 is a two-dimensional schematic drawing showing an instance of preferred orientation of fine granules which might be caused by pressing sample material with a glass plate. FIG. 3 is a two-dimensional representation which schematically illustrates the more desireable condition of low preferred orientation, otherwise known as "highly random crystal orientation". The configuration shown in FIG. 3 may be prepared by dusting a tiny amount of fine sample material particles onto a greased surface. As can be clearly seen from the figures, the dusted sample shown in FIG. 3 has a much more random orientation than the pressed sample shown in FIG. 2, and the pressed sample of FIG. 2 exhibits a much higher pressed orientation than the dusted sample of FIG. 3.

The illustrative examples shown in FIGS. 2 and 3 are only representative of extremely thin layers which would not properly represent bulk materials such as ore tonnages utilized in mineral processing. Accordingly, such methods are not very suitable for minerals processing industries, but are rather much better suited for industries such as cosmetics and pharmaceuticals (where product consistency is tightly controlled and only very tiny amounts of sample material are required since they are much more representative of the material bulk as a whole).

Preferred orientation (i.e. phase identification) is often viewed negatively if present in XRD samples, as it tends to reduce the accuracy of readings. Such errors may ultimately hinder determinations regarding material composition and make-up and lead to inaccurate conclusions. Moreover, for quantitative analysis, it is generally accepted that the measured peak values of reflections (i.e., reflections of type hk0) correspond to or are otherwise indicative of the quantity of the corresponding crystalline phase. Accordingly, for the pressed sample schematically shown in FIG. 2 (which has a higher preferred orientation), reflections of type hk0 would be very low and diminish based on the level of preferred orientation. Conversely, for the dusted sample schematically shown in FIG. 3 (which has low preferred orientation and a highly random crystal orientation), reflections of type hk0 would be higher and increase based on the level of randomness, thereby allowing more accurate determinations about sample material composition.

Several XRD sample preparation systems are already on the market; however, they fail to address objects of the present invention discussed hereinafter. Of these conventional sample preparation systems on the market, Polysius (ThyssenKrupp) offers the Polab® APM Automatic Sample Preparation Module. The Polab® APM basis module consists of a sample loader for blind sample and main sample, a grinding aid dosing unit, a patented grinding unit, and a pellet press.

Herzog offers the HP-PD6 automated press for use with dry powder having a grain of 90 µm. The HP-PD6 applies a "back-loading" pressing process in order to reduce the possibility of adverse influences on prepared pressed samples. The HP-PD6 comprises six stations for pressing samples into steel rings with an aluminum backing. No binder is used, and the press taps the sample gently into the aluminum ring, which aims to reduce preferred orientation, so that it can be used for XRD analysis. In use, a correct dosage of sample material is placed in a ring, residual sample material is "wiped" off from the ring, the sample material is pressed into the ring, and then the ring is then placed on a conveyor belt.

Essa Australia (now a subsidiary of FLSmidth, the Applicant) offers the semi-Automated XRD Press. The Essa® XRD Press is designed to semi-automate the preparation of pressed powder samples for analysis by XRD. A pneumatic piston forms a lightly pressed sample into a two piece sample holder associated with standard XRD analyzers. A sample ring is loaded onto a table and a press is operated to lower a platen. At such a point in time, sample material is placed into the ring. An excess of sample material is required to form a proper pressed sample. The press is operated again, and the sample material is lightly pressed. Excess material is automatically scraped off and vacuumed away. The sample material holder base plate is manually snapped into place and the press is operated again. The sample holder assembly (complete with sample) is rotated onto a discharge base and lowered for manual removal. The press returns to its original state.

All well known vendors who supply automated press tools designated as XRD presses use "back"-loading techniques and not "front"-loading techniques, in order to maximize accuracy of XRD measurements of the samples. However, any gains in accuracy are offset by low sample preparation throughput. Additionally, the back-loading techniques used by all prior XRD sample preparation apparatus require additional complicated sample hardware, since more elements and steps are required to prepare a sample when the measured surfaces of a pressed sample are formed at the bottom of a mold (i.e., blindly formed). This means that more cleaning is necessary, more consumables are required, and more human intervention is necessary. The aforementioned reduces throughput and increases cost.

Although back-loading techniques are widely-accepted as the industry standard, they can only try to reduce instances of preferred orientation phenomena. It is important to note that back-loading techniques do not completely eliminate the phenomenon of preferred orientation. Rather, trade-offs between sample throughput and the amount of preferred orientation present in samples are made during back-loading sample preparation. Moreover, higher variations in crystallographic planes are noticed with back-loading techniques when analyzed over a phi rotation. This yields signal curves which have sinusoidal patterns and unexplained noise— likely due to manual intervention error. See, for example, FIGS. 26 and 27, which show direct comparisons of 4 identical material samples using back-loading (FIG. 26) sample preparation techniques compared to the novel front-loading techniques discussed herein (FIG. 27). As shown in FIG. 27, both quartz samples 1511, 1512 and a mica sample 1513 prepared according to aspects of the invention demonstrate a more uniform distribution than the quartz samples 1501, 1502 and mica sample 1503 shown in FIG. 26, which were prepared using conventional back-loading techniques. It may be appreciated that the non-uniform distributions shown in the back-loading data of FIG. 26 might be attributed to a combination of varying pressure during back loading and non-homogeneous orientation.

Other disadvantages of manual back-loading techniques, include the 'human' factor. In many instances, there will always be too many discrepancies with respect to the reproducibility of collected intensities for samples prepared out of the same material. Differences in results may become even larger, if the samples are prepared at different times and/or by different operators.

Another example of a negative effect attributed to manual back-loading is the formation of preferred oriented domains of crystals in cases of human operators (see graph in FIG. 26). The oriented domain formation is not only limited to minerals that show a strong tendency for preferred orientation, but may also be detectable in other minerals that are harder than the surrounding matrix and might exhibit prominent shapes (e.g. quartz). This formation effect may be completely reduced to a statistical presentation of all phases using the novel apparatus and methods described hereinafter.

Transmission/reflection holders are alternative devices which have also been used to reduce preferred orientation during the preparation of XRD samples—particularly thin films and flat samples. Examples of transmission holders may be found in products manufactured by PANalytical and Bruker. In use, sample material is held between two X-ray films and XRD measurements are performed on the sample using a 2-dimensional (2D) or 3-dimensional (3D) detector. However, such devices are only useful with samples comprised of materials (e.g., organics) which allow X-rays to pass. Unfortunately, materials such as crushed mineral-laden ore used in minerals processing are too dense to allow X-rays to pass and be detected, and they are good absorbers of X-rays. Accordingly, only extremely small quantities of finely-ground ore material can be used in samples for a transmission/reflection holders. As previously mentioned, very small samples of ore are not entirely representative of the bulk material in a mountainside, and therefore, it would be largely impractical to utilize such methods and apparatus in minerals processing industries. Moreover, transmission/reflection holder technologies require intensive manual preparation and are not currently automatable.

OBJECTS OF THE INVENTION

It is, therefore, an object of the invention to provide a mechanically-robust front-loading XRD sample preparation apparatus having a reduced number of sample preparation pieces and elaborate machinery when compared to conventional back-loading devices.

It is an object of the invention to eliminate cumbersome flat bottom knife scraping apparatus commonly found in prior devices.

It is also an object of the invention to provide a more cost effective sample preparation device which requires less maintenance.

It is yet another object of the invention to provide means for quickly and more accurately preparing XRD samples, while lessening and/or eliminating the probability of sample cracking after pressing.

It is a further object of the invention to provide means for automatically/autonomously preparing XRD samples, with little manual intervention.

Another object of the invention is to provide means for quick, reproducible, and repeatable sample preparation for XRD analysis.

A further object of the invention is to reduce occurrences of "preferred orientation", and provide equal or better random crystal orientation than conventional back-loading sample preparation devices.

It is another object of the invention is to provide a front-loading XRD sample preparation system which can be assembled, disassembled, and refurbished much simpler and easier than can be done with existing back-loading apparatus and methods.

Another object of the invention is to provide an XRD sample preparation system which avoids contamination of sample holder bottoms commonly associated with conventional back-loading techniques.

A further object of the invention is to provide an XRD sample preparation system which employs very smooth pressure regulation when pressing sample material.

It is a further object of the invention to provide an XRD sample preparation system which reduces or completely obviates the need for consumables commonly associated with conventional back-loading techniques.

The inventors have set out to build an XRD sample preparation device that challenges the status quo by using innovative "front-loading" technology. During actual reduction to practice, the above objects were achieved by incorporating unique distribution techniques in a novel sample holder design, in combination with a novel leveling device (such as the spreading tool shown in FIG. 12). This innovative "front-loading" technology appeared to significantly minimize surface sample manipulation as will soon be described hereinafter in more detail.

These and other objects of the invention will be apparent from the drawings and description herein. Although every object of the invention is believed to be attained by at least one embodiment of the invention, there is not necessarily any one embodiment of the invention that achieves all of the objects of the invention.

SUMMARY OF THE INVENTION

A sample preparation apparatus which is configured to prepare a material sample suitable for X-ray diffraction is disclosed. The sample preparation apparatus may comprise a dished sample holder bottom that is configured to fit within an annular sample holder. The dished sample holder bottom may have a concave dished surface which is adapted to distribute sample material under pressing forces. In some embodiments, the sample preparation apparatus may further comprise an annular sample holder. In some embodiments, the dished sample holder bottom may be provided within the annular sample holder and configured to move within the annular sample holder in a manner similar to a piston. The dished sample holder bottom may, in certain embodiments, further comprise a seal ring which is disposed between an inner surface of the annular sample holder and an outer surface of the dished sample holder bottom. In some instances, the seal ring may be disposed in a retaining groove provided on the outer surface of the dished sample holder bottom. The retaining groove may be formed of a number of groove surfaces. The seal ring may comprise an outer lip and an inner portion. A recess may be provided between said outer lip and inner portion for added flexibility and/or resilience. In some embodiments, the annular sample holder may further comprise a retaining groove provided at its outer surface which is configured to receive one or more retaining claws. The dished sample holder bottom may be used in a front-loading process. The sample preparation apparatus is generally configured to produce a quality material sample suitable for X-ray diffraction and/or other measuring processes via said front-loading process.

A method of preparing a material sample suitable for X-ray diffraction is also disclosed. The method comprises the steps of dosing a dished sample holder bottom, lightly pressing the sample material, and distributing pulverized sample material within the dished sample holder bottom. The dished sample holder bottom may be configured to fit within an annular sample holder and hold sample material. In preferred embodiments, the dished sample holder bottom has a concave dished surface which is adapted to distribute sample material under pressing forces. In some embodiments, the step of dosing may comprise the use of a dosing funnel. The step of lightly pressing may further comprise avoiding over-pressing of sample material. In some embodiments, the step of lightly pressing may comprise pressing with a flat or textured punch (e.g. a sanded or waffle-patterned punch). All of the method steps may be automated and/or part of a front-loading process. In some instances, dosing steps may involve bringing a leveling device into contact with sample material and rotating said leveling device prior to pressing, in order to increase randomness of crystal orientation. Preferred embodiments of a leveling device may comprise a shaft and a plurality of fingers having different lengths. In some embodiments, distal ends of fingers may be located axially further from a tip at more radially-outwardly portions of the leveling device. In some embodiments, distal ends of fingers may be located axially closer to a tip at more radially-inwardly portions of the leveling device.

A leveling device for a sample preparation apparatus is also disclosed. The leveling device may comprise a shaft having an upper section and a lower section. One or a plurality of fingers may extend from the lower section. In some embodiments, each of a plurality of fingers may have different lengths. For example, distal ends of the fingers may be located further from a tip of the lower section for fingers located at radially outwardly portions of the leveling device. Distal ends of the fingers may be located closer to a tip of the lower section for fingers located at more radially inwardly portions of the leveling device. In some embodiments, the lower section of the leveling device may further comprise one or more openings.

BRIEF DESCRIPTION OF THE DRAWINGS

To complement the description which is being made, and for the purpose of aiding to better understand the features of the invention, a set of drawings illustrating preferred sample preparation apparatus and methods of using the same is attached to the present specification as an integral part thereof, in which the following has been depicted with an illustrative and non-limiting character. It should be understood that like reference numbers used in the drawings may identify like components.

Figure 1:
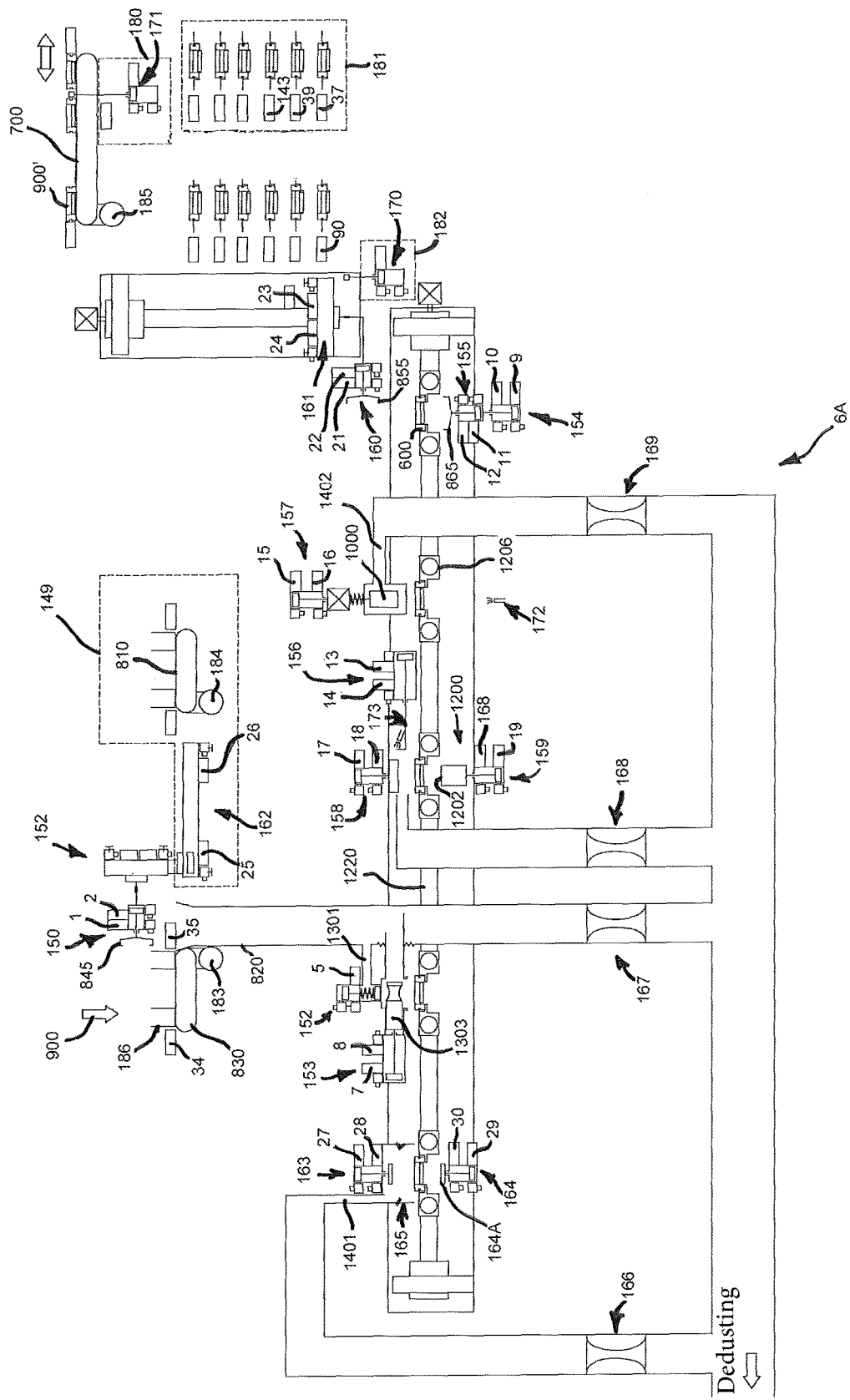
FIG. 1 is a circuit diagram of an XRD sample preparation apparatus according to some embodiments.

In the following, the invention will be described in more detail with reference to drawings in conjunction with exemplary embodiments.

DETAILED DESCRIPTION OF THE INVENTION

Due to the aforementioned disadvantages of back-loading techniques, and for at least the reason that back-loading techniques have several disadvantages which challenge its use in automated processes (e.g., contamination of sample holder bottom, and/or manipulations to the sample), a highly-repeatable, low-contamination, novel front-loading technique has been developed. The novel front-loading technique may provide consistency in producing non-cracking pressed samples without the necessary consumables and elaborate machinery required by conventional back-loading apparatus.

Finely ground sample material 900 is provided to a dished sample holder bottom 500 using a dosing funnel 1304, which places the finely ground sample material 900 at the center of an annular sample holder 400. The sample material 900 may be obtained from a lower hopper portion of a chute 820 which is loaded autonomously via a robotic arm 840. The robotic arm 840 may have pincers 845 which engage a cup 186 containing sample material 900 and remove it from an input conveyor 830. In addition or alternatively to the robotic arm 840, an optional hand sampling conveyor 149 system may be provided, wherein a cup of sample material may be manually inserted by operations personnel. The dished sample holder bottom 500 may be provided with an annular sample holder 400 as an assembly 600. Empty sample holder assemblies 600 may be readily obtained from one or more optional magazines 181 having one or more storage locations 39, 37, 40, 143. In the example shown, there may be up to 12 magazine positions possible. Assemblies 600 may be subsequently cleaned at a cleaning stage using various apparatus 163, 164, 165. A second set of robotic pincers 855 may be used to index the magazine 181 and bring a sample holder assembly 600 onto a movable platform 1206 which is capable of securing the assembly 600 thereto via a number of clamps or retaining claws 1204. A third set of pincers 865, when activated, may toggle/untoggle spring-loaded holding claws 1204 for securing a sample holder assembly 600 to the platform 1206 or releasing a sample holder assembly 600 from the platform 1206. The retention claws 1204 may be spring-biased radially-inwardly and engage a retaining groove 403 located on an outer surface 402 of the assembly 600. The movable platform 1206 may ride along a track 1220 which brings the assembly 600 to different stations within the sample preparation apparatus 6B.

After cleaning and dosing, a pressed material sample 900' is ultimately formed by pressing the dished sample holder bottom 500 against a stationary flat or textured punch 1100 by virtue of movement of the dished sample holder bottom 500 towards said stationary flat or textured punch 1100. An upper exposed measuring surface is subsequently formed at the interface or junction of the finely ground sample material 900, where it contacts the stationary flat or textured punch 1100. The stationary flat or textured punch may comprise a textured lower surface (e.g., sanded, dimpled, gritty, or waffle-patterned) which engages, contacts, and applies light pressing forces to the finely ground sample material 900 as components of a lower press 1200 lift the dished sample holder bottom 500 towards the punch. This creates upper measuring surfaces on the pressed sample briquette 900' which exhibit a reduced preferred orientation. In preferred embodiments, the formed measuring surfaces of the pressed material sample 900' are generally provided on the top side of the pressed material sample 900' that came into contact with the stationary flat of textured punch. Due to the concave dished surface 501 and curved nature of the dished sample holder bottom 500 and its ability to move up and down within the annular sample holder 400, pressure is not particularly applied directly to or solely to portions of the finely ground sample material 900 which ultimately form the measuring surfaces of the pressed material sample 900'. Rather, a majority of the light pressure is applied to the movable bottom part 500 of the sample holder assembly 600 and the measuring surfaces of the pressed material sample product 900' are formed by mere touching/indirect forces only.

Figure 12:
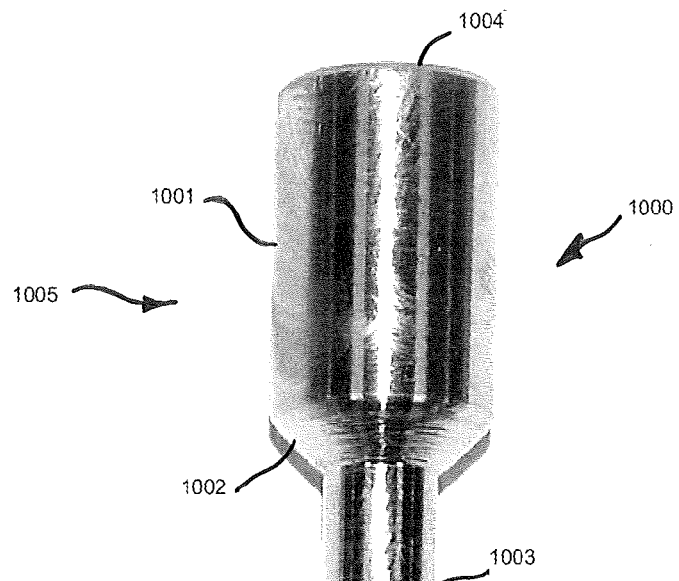
FIG. 12 is a photograph of a leveling device according to some embodiments.
Figure 12:
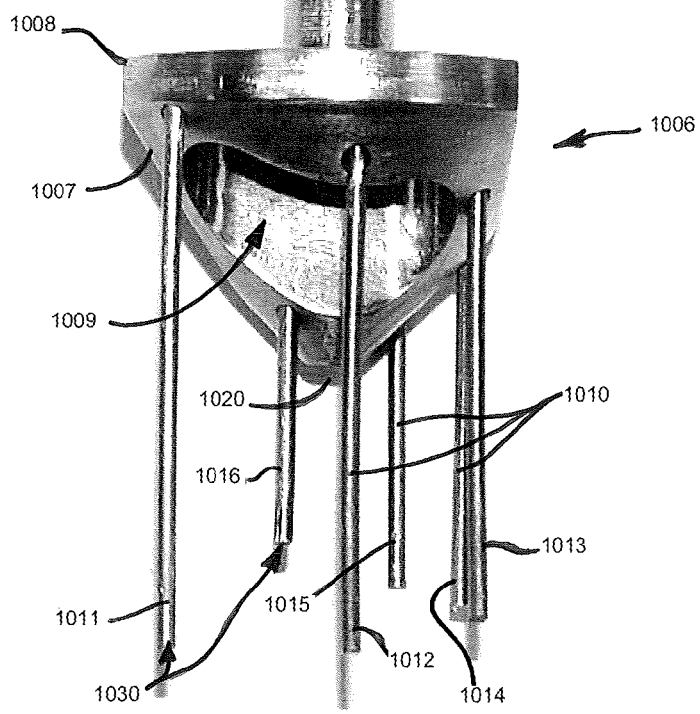

Prior to pressing, a leveling device 1000 may be used to further increase random crystal orientation and disturb the dosing of sample material 900. As the material 900 is applied to the concave dished surface 501 of the dished sample holder bottom 500, it piles up in a mound inside of the sample holder assembly 600. Preferably, as shown in FIG. 12, the leveling device 1000 comprises a number of fingers 1010 which can be driven into surface portions of the formed pile of sample material 900. The leveling device 1000 may lowered into the material 900 by a device 157 and rotated within the dosed sample material 900 to disrupt the material 900, even material distribution, and reduce occurrences of preferred orientation prior to pressing. Pressed sample briquettes 900' may be lifted in their respective sample holder assemblies 600 by pincers 855, and placed on a finished sample conveyor 700. A stopper mechanism 171 may index individual pressed samples 900' and/or prevent them from falling off the conveyor 700.

FIG. 1 is a diagram of an XRD sample preparation circuit 6A according to some embodiments. The circuit 6A comprises a number of digital inputs, digital outputs, controllers, valves, motors, and optional steps/equipment. The circuit 6A is representative of the functionality of an XRD sample preparation system 6B shown in FIG. 28. In the shown preferred embodiment, the circuit 6A comprises a number of digital inputs, including a first digital input 1 for closing cup pincers 845 in a closed initial position, a second digital input 2 for opening cup pincers 845 to release a cup 186 of sample material, a third digital input 5 for a leveling device 1000 such as a doser beater in an initial position, a fourth digital input 7 for a leveling device such as a doser beater in an initial position above a sample holder assembly 600 or empty cartridge 1206, a fifth digital input 8 for a leveling device 1000 such as a doser beater in a bypass position, a sixth digital input 9 for an initial down position of a cartridge pincers 865 lift, a seventh digital input 10 for an up position of a cartridge pincers 865 lift, an eighth digital input 11 for closing cartridge pincers 865 into an initially-closed position to grasp a cartridge 1206 or portions thereof such as claws 1204, a ninth digital input 12 for opening pincers 865 to release a cartridge 1206 or portions thereof, a tenth digital input 13 for pushing a cartridge press cleaner 156 into a pushed-in initial position, a eleventh digital input 14 for pushing a cartridge press cleaner 156 into a pushed-out position, a twelfth digital input 15 for a sample preparation lift 157 in an initial up position, a thirteenth digital input 16 for a sample preparation lift 157 in a down position, a fourteenth digital input 17 for an upper cartridge press 158 in an initial up position, a fifteenth digital input 18 for an upper cartridge press 158 in a down position to set the stationary punch 1100 into position, a sixteenth digital input 19 for a lower cartridge press 159 in an initial down position, a seventeenth digital input 20 for a lower cartridge press 159 in an up position, an eighteenth digital input 21 for output sample pincers 160 in an initial closed position to grasp a sample holder assembly 600 holding a pressed sample 900', a nineteenth digital input 22 for output sample pincers 855 in an open position to release a sample 900', a twentieth digital input 23 for moving output sample pincers 855 into an initial position for cartridge preparation, a twenty-first digital input 24 for moving output sample pincers 855 into an output position, a twenty-second digital input 25 for moving input cup pincers 845 into an initial position for robot input, a twenty-third digital input 26 for moving (via 162) input cup pincers 845 into position for hand sampling input 149, a twenty-fourth digital input 27 for a cartridge preparation cylinder 163 in an initial up position, a twenty-fifth digital input 28 for a cartridge preparation cylinder 163 in a down position, a twenty-sixth digital input 29 for a sample ejector 164 in an initial down position, a twenty-seventh digital input 30 for a sample ejector 164 in an up position, a twenty-eighth digital input 34 for when a cup 186 on a robot cup conveyor 830 is present and in position for a robot arm 840, a twenty-ninth digital input 35 for when a cup 186 on a robot cup conveyor 830 is present and in position for pincers 845, a thirtieth digital input 37 for when a cup 186 on a cartridge conveyor 830 is present and in position for pincers 845, a thirty-first digital input 39 for when a cup on a hand sample cup conveyor 810 is present and in position for pincers 845, and a thirty-second digital input 40 for when a cartridge is present within a first cartridge holder (e.g., holder No. 1)

The circuit 6A may further comprise one or more controllers, such as a stepper controller 143 for a stepping motor that moves cartridges and limits positions for sample taking, or a stepper controller 144 for a stepping motor that moves cartridges and limits positions for cleaning.

The circuit 6A may further comprise one or more valves, including a first valve 150 for inputs to cup pincers 845 which is configured to grasp or release a cup 186, a second valve 151 for inputs to cup discharging which is configured to discharge or not discharge a cup, a third valve 152 for turning on a leveling device 1000 such as a doser beater, a fourth valve 153 for bypassing a doser and placing a cartridge into a bypass position, a fifth valve 154 for lifting cartridge pincers into an up or down position, a sixth valve 155 for closing or opening cartridge pincers, a seventh valve 156 for pushing out a cartridge press cleaner, an eighth valve 157 for placing a sample preparation lift into a down position, a ninth valve 158 for putting an upper cartridge press into a down position, a tenth valve 159 for positioning a lower cartridge press into an up or down position, an eleventh valve 160 for putting output sample pincers in an closed or open position, a twelfth valve 161 for keeping output sample pincers moving and in position for cartridge preparation output, a thirteenth valve 162 for keeping input cup pincers 845 moving and in position for robot 840 or manual 149 (i.e., "hand") input, a fourteenth valve 163 for putting a cartridge preparation cylinder into a down position, a fifteenth valve 164 for putting a sample ejector into an up position, a sixteenth valve 165 which turns cartridge cleaning jet air on, a seventeenth open valve 166 for cleaning dedusting, an eighteenth open valve 167 for dosing dedusting, a nineteenth open valve 168 for press dedusting, a twentieth open valve 169 for sample preparation dedusting, a twenty-first valve 179 for putting a cartridge lift stopper into an up position or a down position, wherein the up position may be an initial position, a twenty-second valve 171 for placing a cartridge conveyor stopper into up and down positions, wherein the up position may be an initial position, a twenty-third valve 172 for turning on sample preparation jet air, and/or a twenty-fourth valve 173 for turning on cartridge press cleaner jet air.

Dashed boxes 149, 180, 181, 182 within the circuit 6A indicate optional configurations. For example, reference numeral 149 indicates an optional hand-sampling step; it allows laboratory personnel to manually insert a cup with sample material while the apparatus 6B is in automatic mode, without disruption of automatic line. Reference numeral 180 indicates an option for use with a robot laboratory. Option 180 comprises a stopper mounted on a conveyor belt 700. The stopper 180 provides two positions for sample holder assemblies 600. A first outer (at the end of belt) position may be designed for robot (insertion) placing of a dosed and/or measured sample holder assembly; and a second position may be designed for robot moving a holder 600 with prepared sample 900'. Without option 180, an annular sample assembly 600 may go onto the conveyor belt directly to a defined position. The non-limiting shown configuration is for a (non robotic) conveyor belt automation laboratory feeding systems. Reference numeral 181 indicates an option for increasing position number in magazine from 6 to 12 positions by adding a second column of positions to the magazine. Reference 182 indicates an option which may be installed when option 181 is used. Option 182 includes a stopper 170 which stops a manipulator of assemblies 600 located in the second column of the magazine 181. One or more motors 183, 184, 185 may be utilized with conveying mechanisms to deliver sample material, annular sample holders 600, sampling equipment, or components within the circuit 6A, without limitation. A cup 186 containing sample material may be introduced and/or moved within the circuit 6A manually or automatically.

Figure 2:
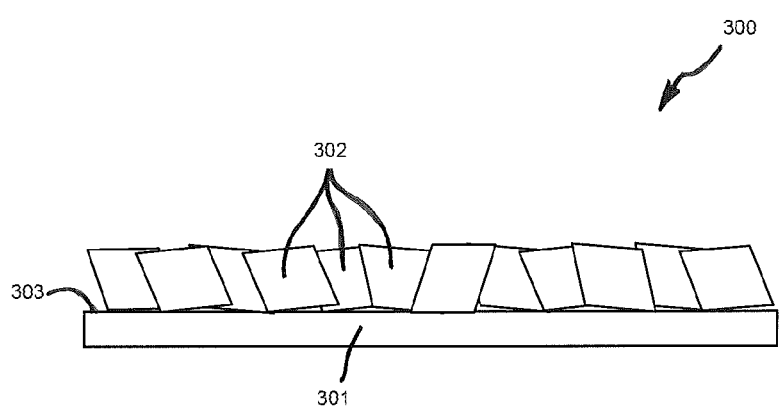
FIG. 2 is a 2-D schematic representation of a material sample formed by pressing with a glass plate which demonstrates the phenomenon of preferred orientation.

FIG. 2 is a 2-D schematic representation of a material sample formed by pressing with a glass plate 301 which demonstrates the phenomenon of preferred orientation. A thin layer of sample material 300 is pressed against a surface 303 of a glass plate 301. This yields crystals 302 which have highly-preferred orientations. It should be understood that different sample materials may exhibit different preferences for position. For example, sample materials 302 which possess flat/tabulate or needle-like crystallography will likely align with a preferred orientation when forced (See FIG. 2)

Figure 3:
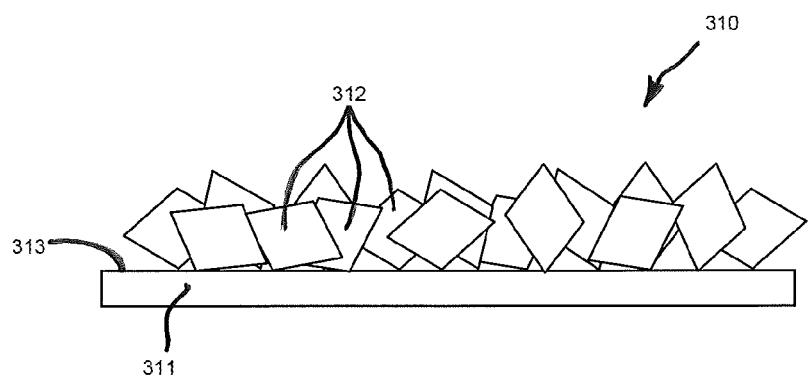
FIG. 3 is a 2-D schematic representation of a material demonstrating the phenomenon of low preferred orientation or highly randomized crystal orientation.

FIG. 3 is a 2-D schematic representation of a material sample formed by dusting a greased surface 313 of a plate 311 with a thin layer of dusted material sample 310. FIG. 3 demonstrates the phenomenon of low preferred orientation or highly randomized crystal orientation, wherein crystals 312 are shown to be arranged or otherwise configured with random orientations.

Figure 4:
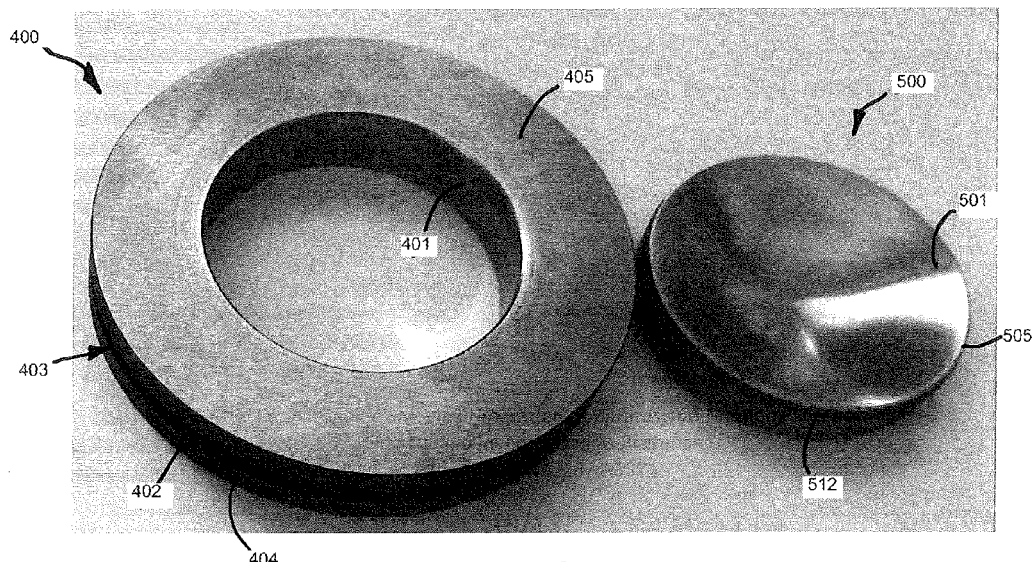
FIG. 4 is a photograph showing separated components of an XRD sample holder preparation apparatus prototype according to some embodiments.
Figure 5:
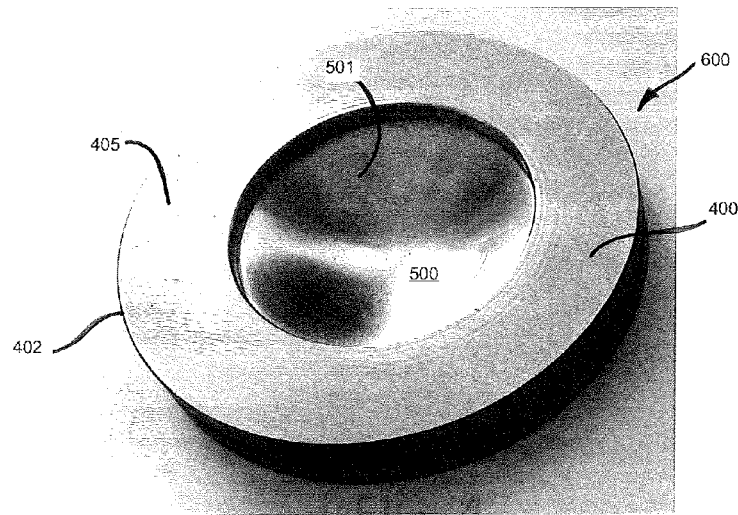
FIG. 5 is a photograph showing the separated prototype components of FIG. 4 in an assembled configuration according to some embodiments.
Figure 6:
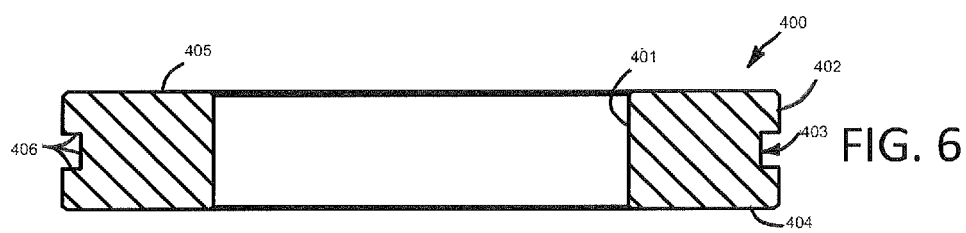
FIG. 6 is a cross-sectional view of an annular sample holder according to some embodiments.
Figure 7:
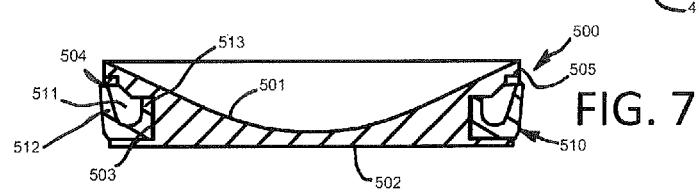
FIG. 7 is a cross-sectional view of a dished sample holder bottom according to some embodiments.
Figure 8:
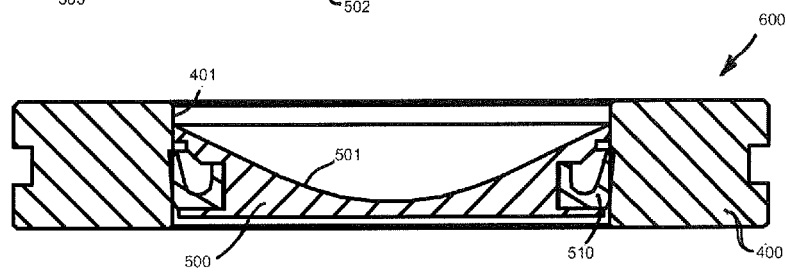
FIGS. 8 and 9 show an assembly of the annular sample holder shown in FIG. 6 and the dished sample holder bottom shown in FIG. 7 according to some embodiments.
Figure 9:
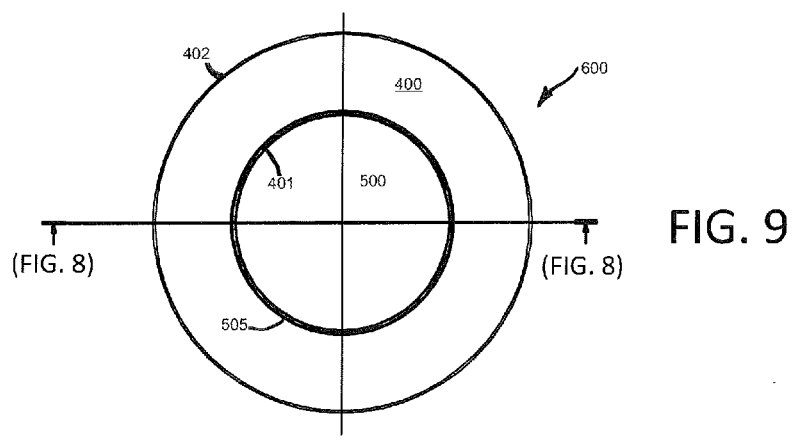

FIG. 4 is a photograph showing components of an XRD sample preparation apparatus prototype according to some embodiments. Shown, is an annular sample holder 400 having a radially inner surface 401, a radially outer surface 402 having a retaining groove 403, a lower (e.g., planar) surface 404, and an upper (e.g., planar) surface 405. In some preferred embodiments, such as the one shown, the annular sample holder 400 may be configured with symmetry so as to be able to be used in the same manner regardless of which of the surfaces 404, 405 are upright on the platform 1206. Also shown in FIG. 4, is a dished sample holder bottom 500 having a radially outer surface 505, a concave dished surface 501, and an outer lip 512 which is preferably flexible. FIG. 5 is a photograph showing the separated prototype components of FIG. 4 in an assembled configuration according to some embodiments. Shown, is a sample holder assembly 600 which comprises the dished sample holder bottom 500 movably inserted within the inner surface 401(FIG. 4) of the annular sample holder 400. FIGS. 6-9 show the annular sample holder 400, dished sample holder bottom 500, and assembly 600 thereof in more detail. FIG. 6 is a cross-sectional view of an annular sample holder according to some embodiments. FIG. 7 is a cross-sectional view of a dished sample holder bottom according to some embodiments. As shown in FIGS. 7 and 8, the dished sample holder bottom 500 may comprise a lower (e.g., planar) surface 502, a groove 503 for receiving a seal ring 510, and a clearance 504 portion adjacent the groove 503 for accepting flexing of the outer lip 512 of said seal ring 510. Seal ring 510 comprises an inner portion 513, and a recess 511 between said inner portion 513 and lip 512. Groove surfaces 406 may be provided within the retaining groove 403 of the annular sample holder 400 and serve as surfaces for engaging a retaining claw 1204 as will be discussed hereinafter in reference to FIG. 18. FIGS. 8 and 9 show a combination of the annular sample holder 400 shown in FIG. 6 and the dished sample holder bottom 400 shown in FIG. 7 according to some embodiments.

The concave dished surface 501 provided to the dished sample holder bottom 500 has many advantages over a flat surface. Mechanical tests performed by the inventors exhibited huge advantages for the concave dished surface 501, including better pressure distributions before pressing (e.g., during dosing), better pressure distributions during pressing, and better pressure distributions after pressing—leading to less cracked pellets 900'. It is apparent that due to the convex surface 502, layer height of the material 900 increases towards the center of the sample holder 600. The concave dished surface 501 may comprise many shapes, including ovular shapes, egg-shaped profiles, 3D curves, paraboloids, and/or convex shapes in any configuration, without limitation. In some instances, the smoothness of the concave dished surface 501 may be varied, or the concave dished surface 501 may be formed from, defined by, or otherwise closely approximated by a series of many small, high resolution, step features.

Figure 10:
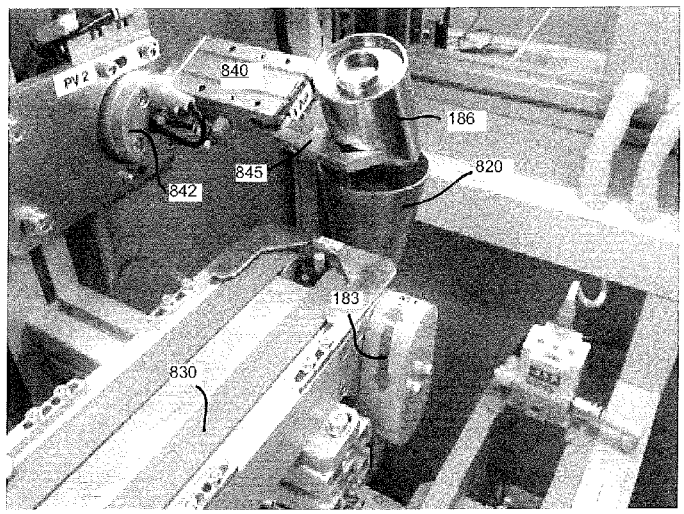
FIG. 10 is a photograph showing automated filling of a chute with sample material according to some embodiments.
Figure 11:
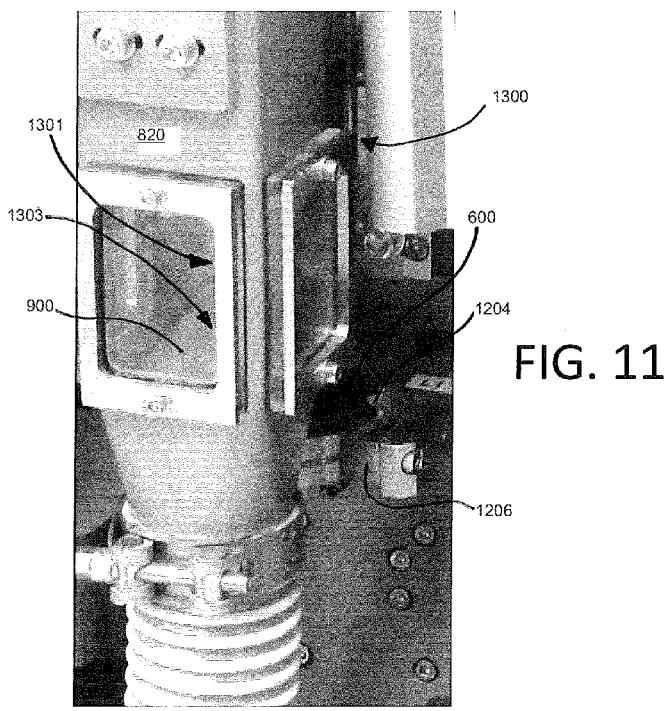
FIG. 11 shows a dosing step which provides a predetermined amount of sample material to the sample holder assembly shown n FIGS. 8 and 9.
Figures 19, 20:
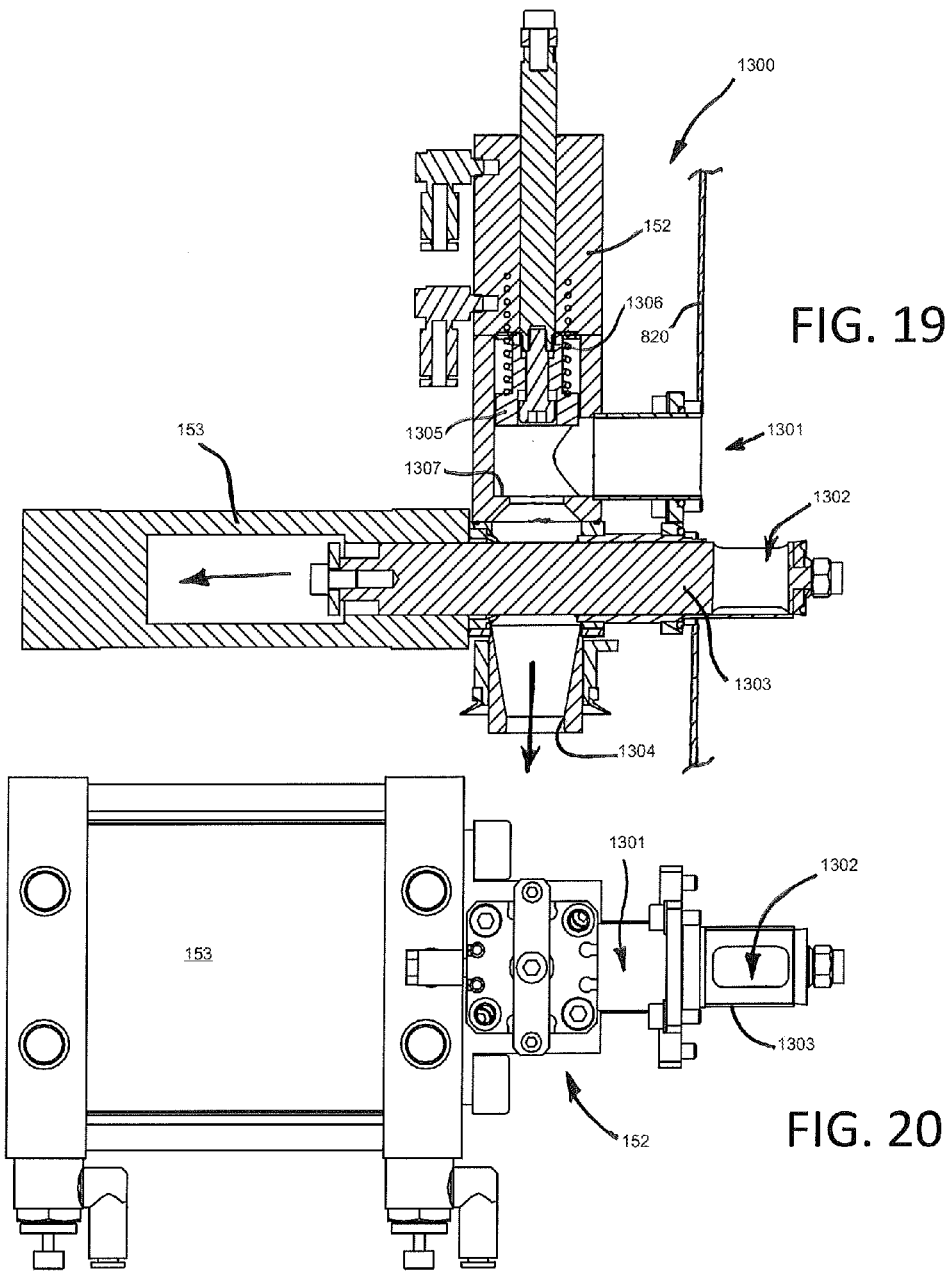
FIGS. 19-25 show various views of XRD sample preparation apparatus components according to some embodiments.

FIG. 10 is a photograph showing a part of material filling/dosing unit in ASP100 which incorporates a chute 820 according to some embodiments. First, a cup containing powdered sample material 186 is moved along a robot cup conveyor belt 830 (via motor 183), and is picked up by a robot arm 840 connected to the apparatus 6B by a joint 842. Then, pincers 845 located on the robot arm 840 are used to dump sample material 900 contained within the cup 186 into the chute 820. Then material goes through an elongate tube structure and ends up proximate a dosing device 1300 and the sample holder assembly 600. A dosing spoon 1302, shown in a taking position in FIG. 19, samples material located within the material chute 820 in a lower hopper section of the chute 820. Valve 153 (FIGS. 1, 19) operates a piston rod 1303 which inserts the dosing spoon 1302 into the chute 820. The chute 820 is preloaded with sample material 900 from cup 186 which has been dumped by robot arm 840. The spoon 1302 brings sample material 900 from the chute 820 into the dosing unit 1300. When the spoon 1302 aligns itself with a dosing funnel 1304, sample material obtained from the chute 820 and contained 900 within the spoon 1302 then goes through the dosing funnel 1304. This causes center portions of the dished sample holder bottom 500 to be dosed with more sample material 900 than outer portions of dished sample holder bottom 500. In some embodiments, only central portions of the annular sample holder 600 which are positioned directly below the dosing funnel 1304 may receive and/or contain sample material 900. FIG. 19 shows dosing device 1300 in a position where the spoon 1302 is extended and configured to obtain sample material 900 from chute 820. FIG. 11 shows a photograph of a sample holder assembly 600 being dosed with an amount of sample material 900 at a lower portion of chute 820.

FIG. 12 is a photograph of a leveling device 1000 according to some embodiments. The leveling device 1000 comprises a series of one or more fingers 1010 (which may be comprised of vertical wires, ribs, protuberances, or teeth-like members) for enhanced sample material distribution within the sample holder assembly 600 after dosing. An equal surface distribution of the sample material 900 is established and maintained by redistributing small portions of sample evenly while minimizing surface impacts of spreading. The fingers 1010 may be configured to gently graze through the dosed sample material 900, comb lightly through portions the sample, or dig deep through the depth core providing movement to all portions of the dosed sample material 900. The particular leveling device 1000 shown serves to minimize scraping of surfaces of both the annular sample holder 400 and dished sample holder bottom 500, and further serves to only disturb surface portions of the dosed sample material 900. This results in both: a level sample for better distribution of pressure, and an enhanced random crystal orientation before pressing.

Figure 13:
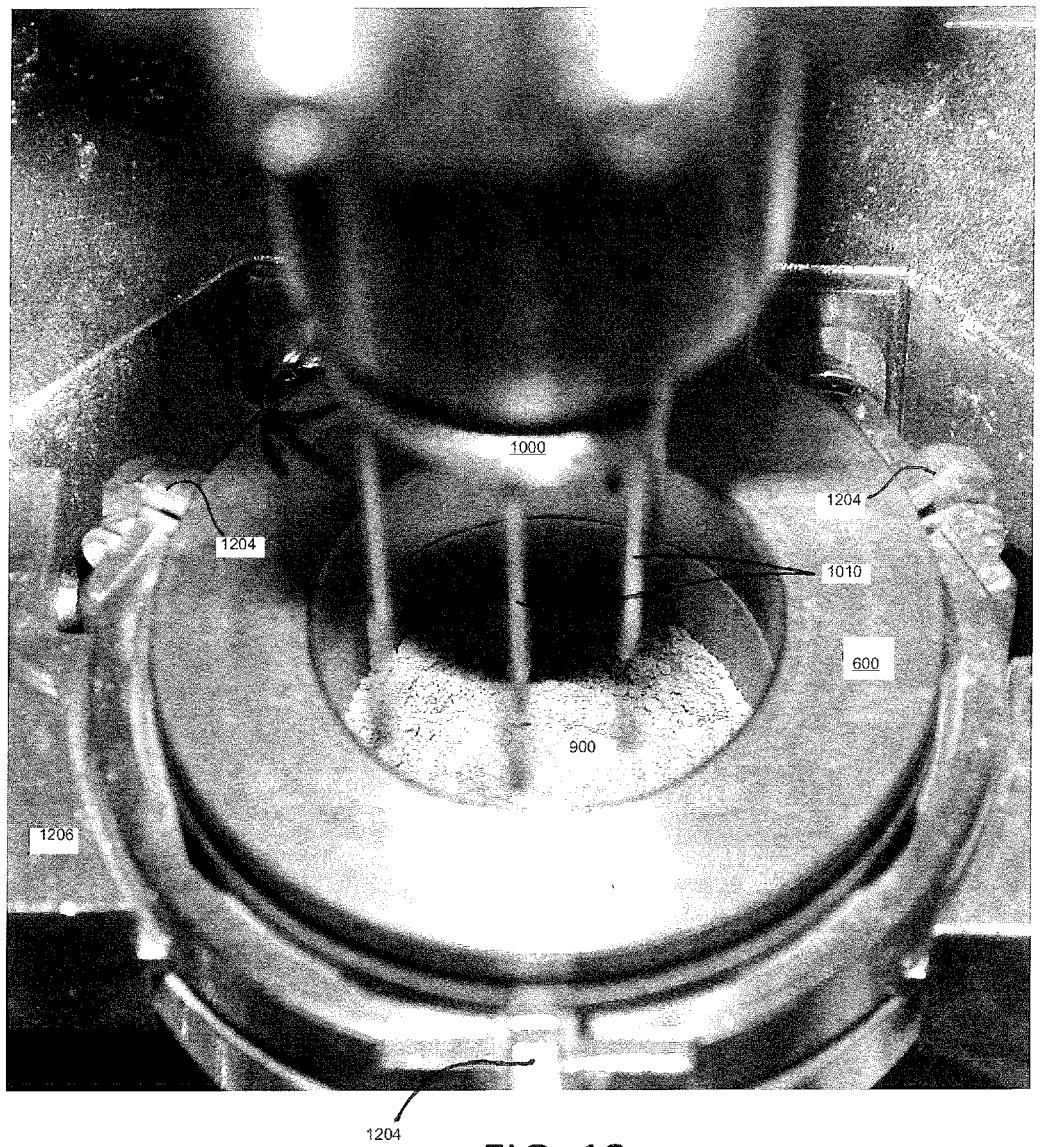
FIG. 13 is a photograph showing a leveling step being performed using the leveling device of FIG. 12.

Turning now to the details of leveling device 1000, a shaft 1003 extends between a top end 1004 and a tip end 1020. Adjacent the top end 1004 is an upper section 1005 having a proximal mount 1001 and taper 1002. Adjacent the tip 1020 is a lower section 1006 having an enlarged upper portion 1008, a tapered surface portion 1007, and one or more openings 1009 therein. Each finger 1010 comprises a finger distal end 1030. In some embodiments, as shown, multiple fingers 1010 may be utilized. In some embodiments the longest finger 1011 may be positioned most radially-outward most location. In some embodiments, the shortest finger 1016 may be positioned at a radially-inward most location on the lower section 1006. In some embodiments, a first finger 1012 may be longer than a second finger 1013, a second finger 1013 may be longer than a third finger 1014, and/or a third finger 1014 may be longer than a fourth finger 1015. In some embodiments, a first finger 1012 may be located further radially-outwardly with respect to a second finger 1013, a second finger 1013 may be located further radially-outwardly with respect to a third finger 1014, and/or a third finger 1014 may be located further radially-outwardly with respect to a fourth finger 1015. FIG. 13 is a photograph showing a leveling step being performed using the leveling device 1000 of FIG. 12 and other XRD sample preparation apparatus (e.g., sample holder assembly 600) according to some embodiments.

Figure 14:
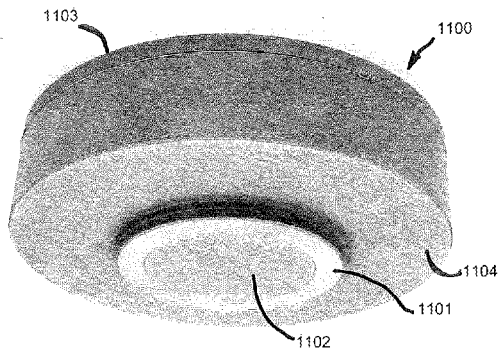
FIG. 14 shows a punch device for an XRD sample preparation apparatus according to some embodiments.

FIG. 14 shows a flat or textured punch 1100 device which may form a portion of an XRD sample preparation apparatus 6B according to some embodiments. The flat or textured punch 1100 may be a stationary device having a downwardly-facing, substantially flat, sanded, rough, and/or patterned surface (e.g., a "waffle" pattern). In some non-limiting preferred embodiments, the punch 1100 is preferably designed to give a lightly-pressed briquette 900' of sample material a course upper measuring surface. Textured/sanded surface inner parts 1102 of the punch 1100 may advantageously affect the final measuring surface of a pressed briquette 900' sample. In some embodiments, textured/sanded surface inner parts 1102 of a punch 1100 may be configured to rough up or randomly disturb particles of sample material which would otherwise be preferably oriented. In some embodiments, as shown, a textured punch 1100 may be composed of an upper surface part 1103, a lower surface part 1104 having an outer flat ring 1101 and a pressing textured surface part 1102. Optionally, the punch may include a replaceable spare pressing part 1102 with different surfaces designed to compliment different sample materials 900. In cases where a flat punch is used, the punch 1100 may be comprised of a single piece part.

Figure 15:
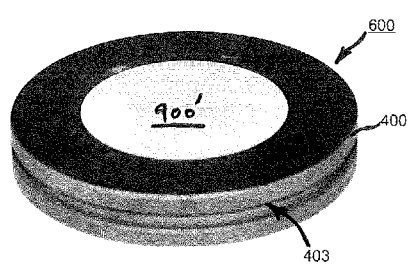
FIG. 15 shows a lightly pressed, prepared XRD material sample pellet formed within an annular sample holder according to some embodiments.

FIG. 15 shows a lightly pressed, prepared XRD material sample pellet 900' formed within a sample holder assembly 600 according to some embodiments. The briquette 900' has an upper exposed measuring surface which is configured to be used in an XRD measuring test. The upper exposed measuring surface demonstrates improved randomness due to the complimentary sanded surface 1102 of the textured punch 1100, and also due to the unique leveling and pressing steps disclosed alone or in combination with a concave dished surface 501 and movable dished sample holder bottom 500 which is designed to move relative to the annular sample holder 400 and take up and evenly distribute pressures during pressing of the sample material 900.

Figure 16:
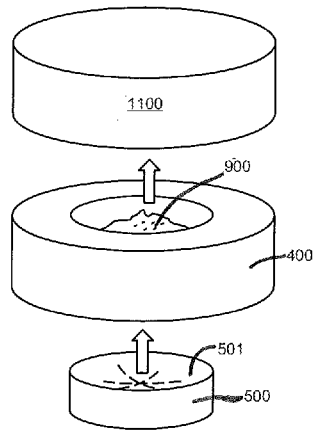
FIG. 16 is a schematic representation of an XRD sample preparation apparatus according to some embodiments.

FIG. 16 is a schematic representation of an XRD sample preparation apparatus according to some embodiments. A dished sample holder bottom 500 fits within the annular sample holder 400, and finely-ground sample material 900 is dosed within the annular sample holder 400 such that it rests on the concave dished surface 501 of the dished sample holder bottom 500. A punch (flat or textured) 1100, which may be stationary, comes into contact with the sample material 900, and applies a force to the sample material 900. The concave dished surface 501 of the dished sample holder bottom 500 evenly distributes the sample material 900 granules around the annular sample holder (i.e., radially outwardly) as pressing forces gradually increase. Since the dished sample holder bottom 500 is movable with respect to the flat or textured punch 1100 and annular sample holder 400, along the same axis, excess pressure exerted by the flat of textured punch 1100 simply moves the granules within the sample holder assembly 600 around (e.g., outward within the annular sample holder 400.

Figure 17:
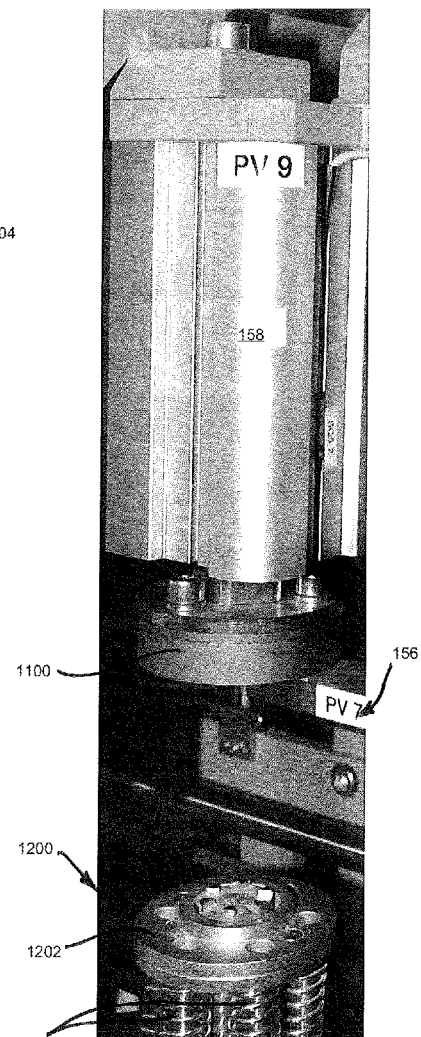
FIG. 17 shows a punch installed above a press which is configured to form a pressed sample briquette.
Figure 18:
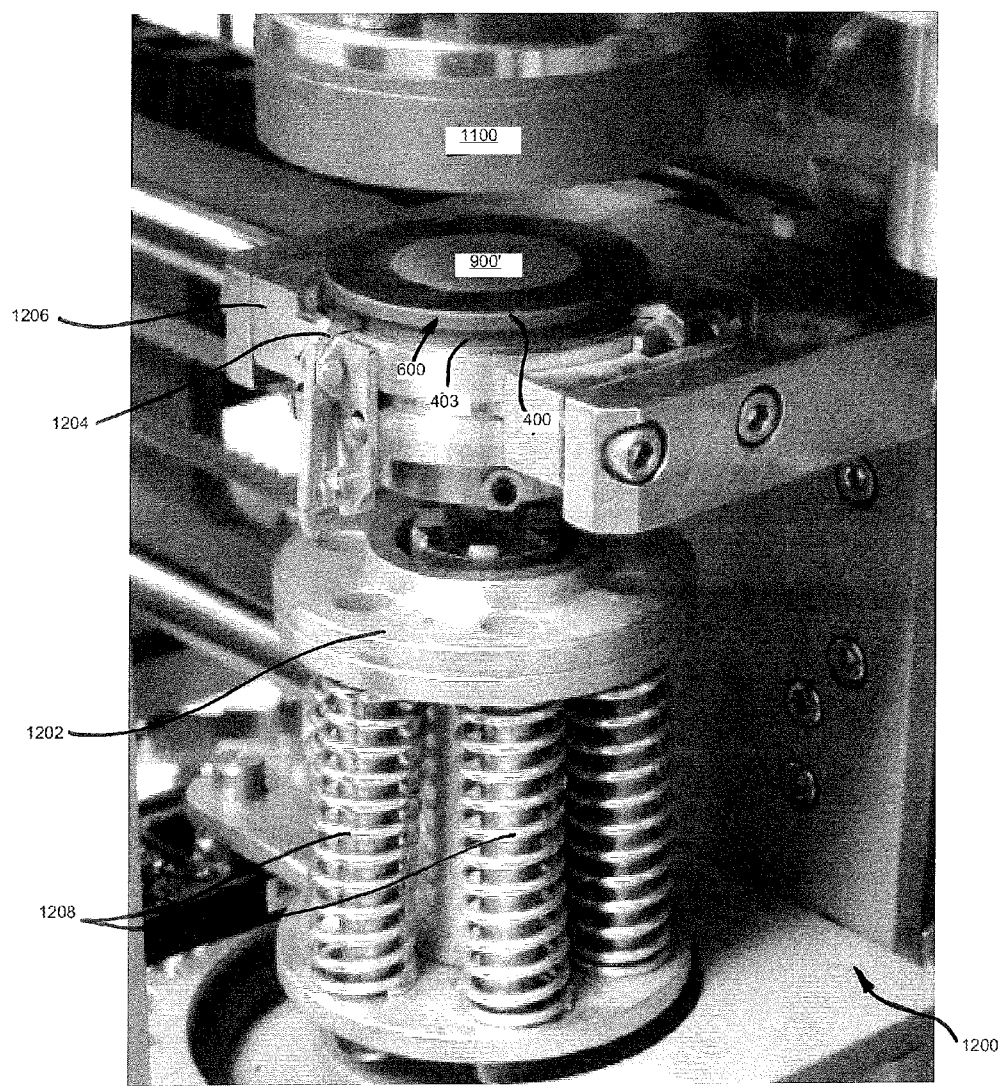
FIG. 18 is a photograph of a lightly-pressed an XRD material sample briquette after utilizing the novel sample preparation apparatus described herein.

FIG. 17 shows a textured punch 1100 according to some non-limiting embodiments. The textured punch 1100 id installed above a such as a pneumatic lower cartridge press piston 159. A lower press 1200 having a platen 1202 and one or more springs 1208 may be provided to an XRD sample preparation apparatus 6B. The press 1200 may be a lower cartridge press which moves the platen 1202 and a supported pre-dosed sample holder assembly 600 upwards, towards a flat or textured punch 1100 which may be stationary with respect to other components of the XRD sample preparation apparatus 6B. FIG. 18 is a photograph showing the operation of lightly pressing an XRD material sample utilizing the novel sample preparation apparatus described herein in greater detail. The piston 158 with mounted punch 1100 operated by pneumatic cylinder 158 moves downward to defined position; during pressing, the punch 1100 is fixed in position. One or more retaining claws 1204 engage a retaining groove 403 of the sample holder assembly 600 to secure it to a movable platform/cartridge 1206 which is guided by a track 1220. The pressing forces that are utilized to prepare a completed XRD sample briquette 900' may vary and may range between approximately 0.001 tons to approximately 0.1 tons. Preferably, pressing forces may be chosen to be as close to human hand pressure as possible. According to some non-limiting embodiments, for example, pressing forces used may be chosen between 0.01 tons and approximately 0.1 tons. The data obtained in FIG. 27 was obtained using a pressing load of approximately 0.057 metric tons (57 kg). In some preferred embodiments, the pressure curve over time is gradual and/or comprises small stepwise increments.

Figure 21:
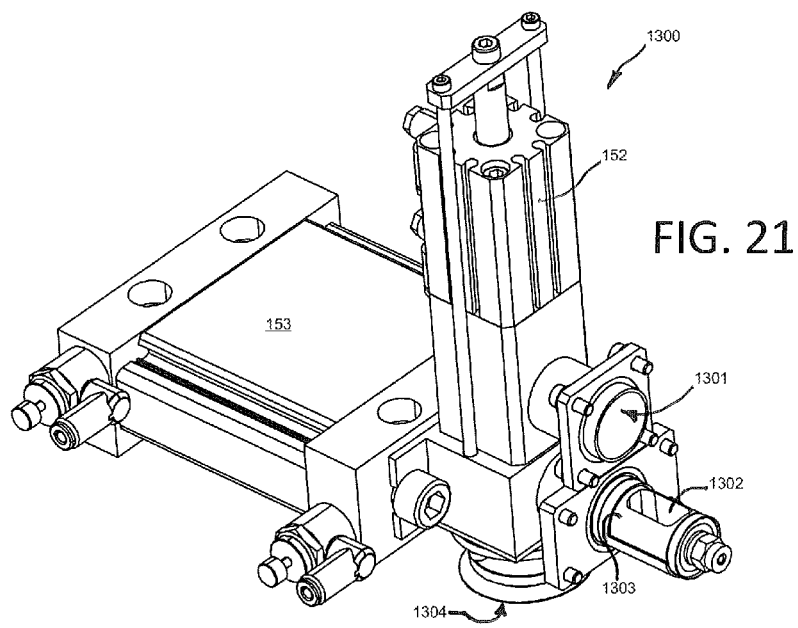

FIGS. 19-25 show various views of XRD sample preparation apparatus components according to some embodiments. FIGS. 19-21 show a dosing unit 1300 comprising a dosing spoon 1302 for sampling material from the material chute 820, a movable piston rod 1303 operated by valve 153 (e.g., a pneumatic cylinder), a dosing funnel 1304, and an exhausting port 1301. Via the exhausting port 1301, the dosing unit 1300 is cleaned—including chute 820, dosing funnel 1304, and dosing spoon 1302. Exhausting port 1301 may comprise a plunger 1305 loaded by a spring 1306 which is configured to contact a plunging surface 1307. The plunger 1305 may be held against the plunging surface 1307 (i.e., in a closed position) during cleaning. The dosing funnel 1304 is preferably conveniently located above a sample holder assembly 600 and it is configured to or otherwise designed to precisely direct sample material 900 to central parts of sample holder assembly 600. FIG. 19 shows a transverse cross-section of a dosing unit 1300 according to some embodiments. FIG. 20 shows the dosing unit of FIG. 19 from a top plan view. FIG. 21 is 3-dimensional isometric view of the dosing unit 1300 shown in FIGS. 19 and 20.

Figure 22:
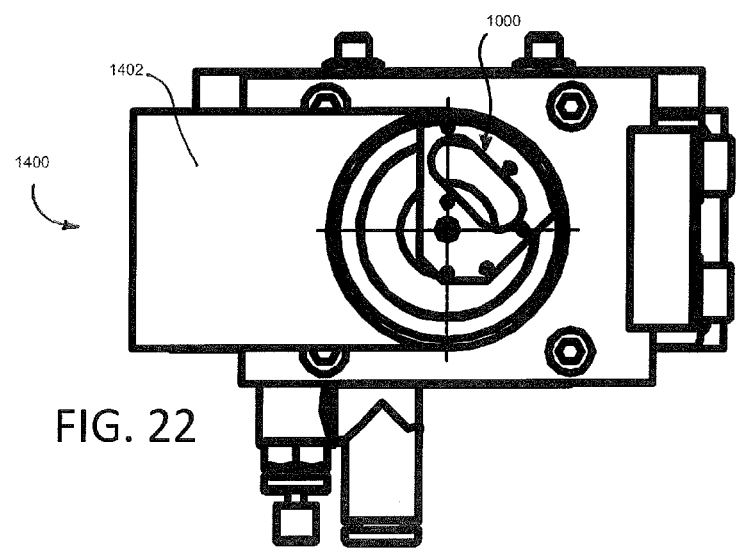
Figure 23:
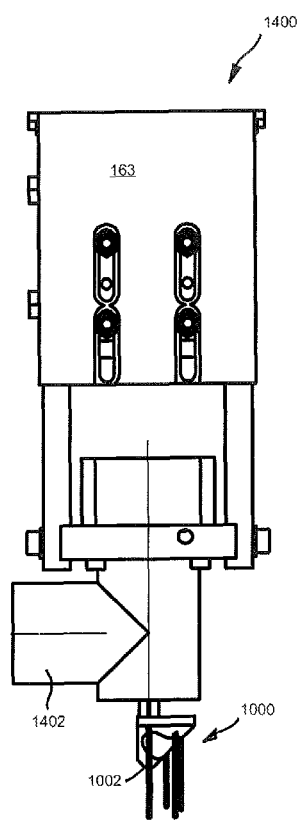
Figure 24:
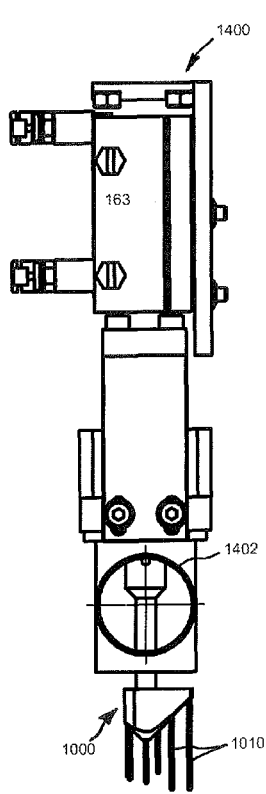
Figure 25:
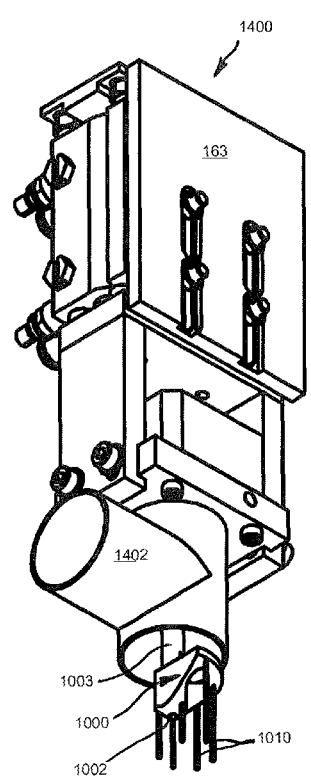

FIGS. 22-25 show a leveling device 1000 in a leveling assembly 1400 and a de-dusting outlet 1402. FIG. 22 shows a "bottom-looking up" view of a leveling assembly 1400, and FIGS. 23 and 24 show the leveling assembly from two different sides, respectively. FIG. 25 shows 3-dimensional isometric view of complete leveling apparatus 1400.

Figure 26:
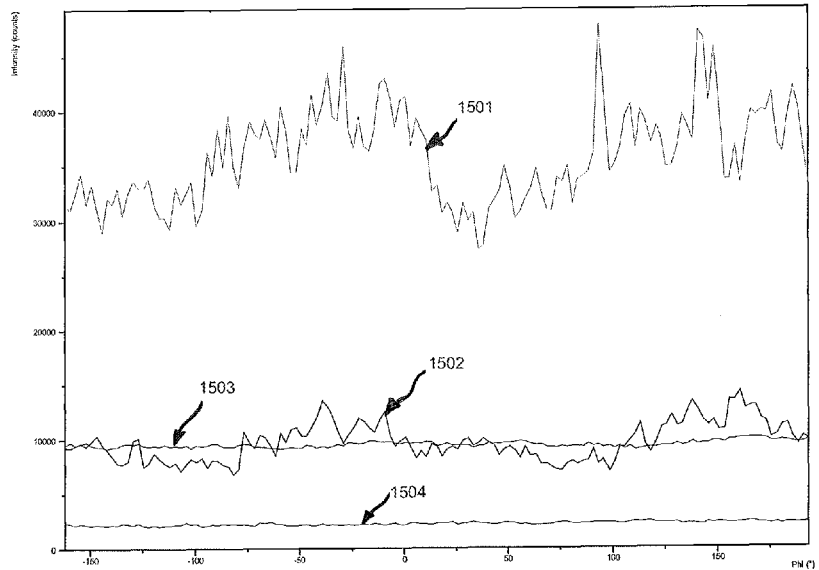
FIG. 26 shows phi rotation measurement result for 4 particular material samples which were carefully manually prepared by an industry expert using widely-accepted back-loading sample preparation techniques.
Figure 27:
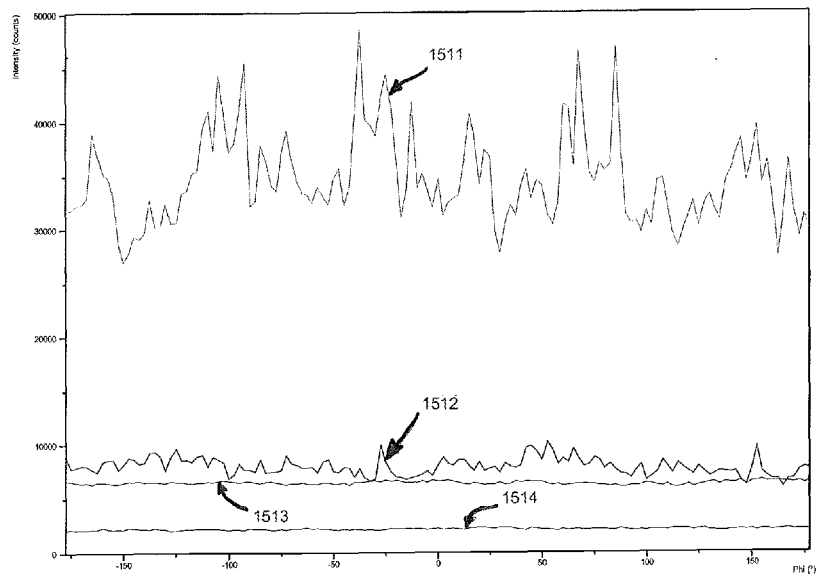
FIG. 27 shows phi rotation measurement results for the same 4 particular samples shown in FIG. 26; however, using the novel automated front-loading apparatus, methods, and techniques described herein.

FIG. 26 shows diffraction results of phi experiment measurements of a powdered rock sample containing 3 different minerals (quartz, mica, and orthoclaise). These were manually prepared by an industry expert using widely-accepted conventional back-loading sample preparation techniques. A Phi rotation test was performed to reveal if the distribution of crystallographic planes for each mineral reflection 1501, 1502, 1503, 1504. Ideally, the lines representing crystallographic planes at varying angle θ would be horizontal (flat)—indicating randomness at every orientation. However, as shown, variations are distinctly present in at least the quartz 1501, 1502 and mica 1503 sample data. These non-uniform distributions may be caused by varying pressure during back-loading and/or non-homogeneous orientation (selective preferred orientation). The mica (muscovite) variety is well-known to exhibit preferred orientation behavior, and this may be a major contributor to the variations in line 1503. FIG. 27 shows a repeated phi measurement results using the novel automated front-loading apparatus and methods described herein. A phi rotation test utilizing preferred embodiments of the invention was performed on the same powdered rock used in FIG. 26. Clearly, the degree of variation and non-uniformity has been reduced as is evident by the flattening of the quartz sample curves 1511, 1502, as well as the mica curve 1513. Any variability associated with hand-pressing has also been reduced. The reduced variations in the mica curve 1513 (as compared to curve 1503) are a strong indication that the invention has enhanced crystallographic representations. No significant differences were observed between the phi rotation results 1504, 1514 for the orthoclase sample.

The inventors obtained third party opinions in order to determine the effectiveness of the XRD sample preparation apparatus described herein. The opinions were based purely on the results shown in FIGS. 26 and 27. Two independent experts from a local university materials research centre (who regularly use state-of-the-art XRD systems from PANalytical (e.g., Empyrean) stated that results shown in FIG. 27 (which were produced in accordance with aspects of the invention) are as good "or even better" than the results shown in FIG. 26 (which were obtained using conventional back-loading techniques). Moreover, a well-recognized, accomplished PhD crystallographer and advanced XRD designer with more than 25 years experience concurred, stating that the results shown in FIG. 27 are "clearly better" than the results shown in FIG. 26.

Figure 28:
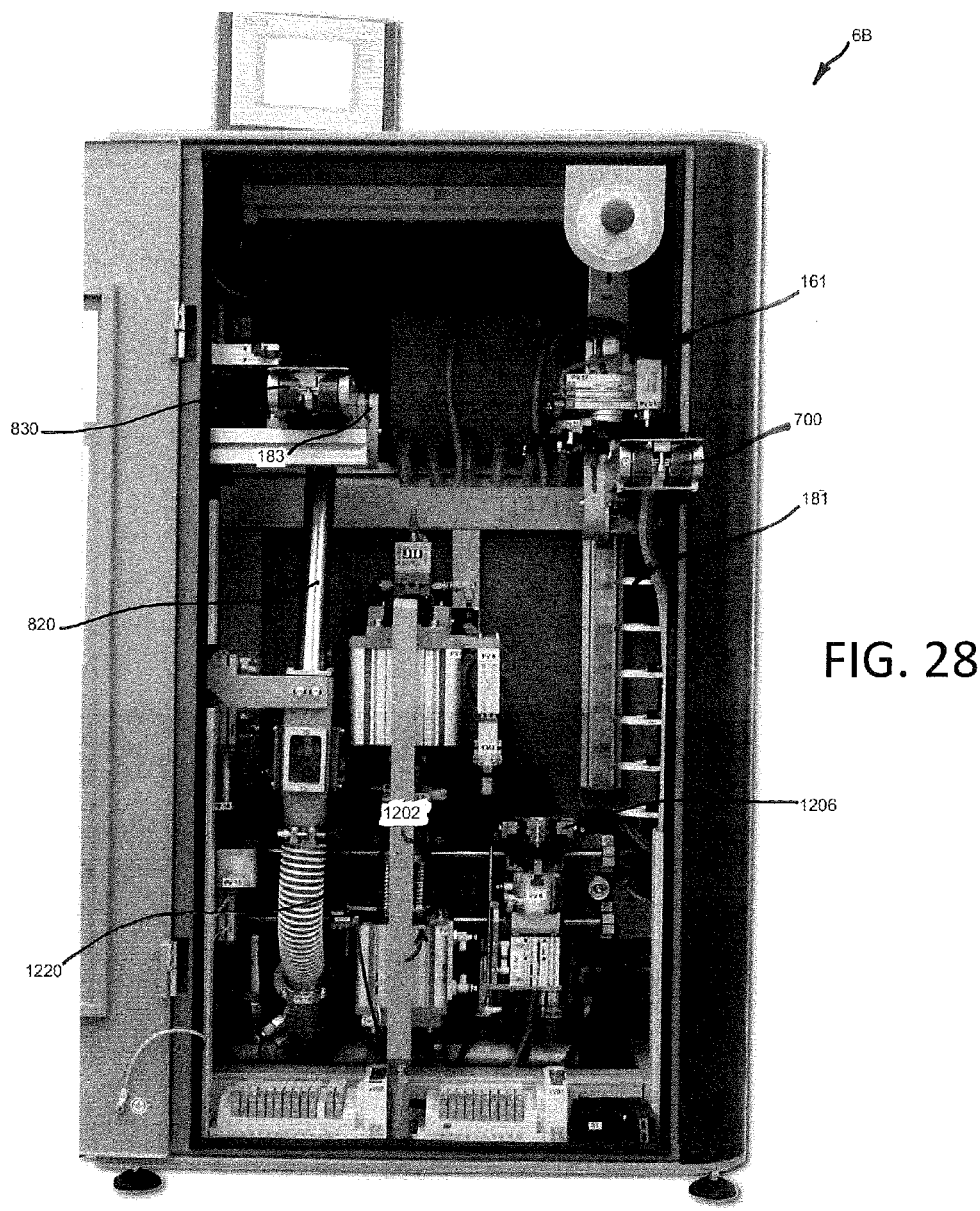
FIG. 28 is a photograph of a functional prototype of a front-loading XRD sample preparation apparatus according to some embodiments, which utilizes the circuit diagram shown in FIG. 1.

FIG. 28 is a photograph of a functional prototype of a front-loading XRD sample preparation apparatus 6B according to some embodiments and which utilizes the circuit diagram shown in FIG. 1. The apparatus shown is a working prototype of a modified FLSmidth® ASP100 soft press device which employs the front-loading methods and apparatus described herein. In some embodiments, soft pressing forces used may be between approximately 0.078 and 0.780 tons (pneumatic) with a calculated effective force range approximating 0.057 to 0.725 metric tons. Of course, some deviations from these pressing forces are anticipated, and may vary depending on sample material 900 type.

Figure 29:
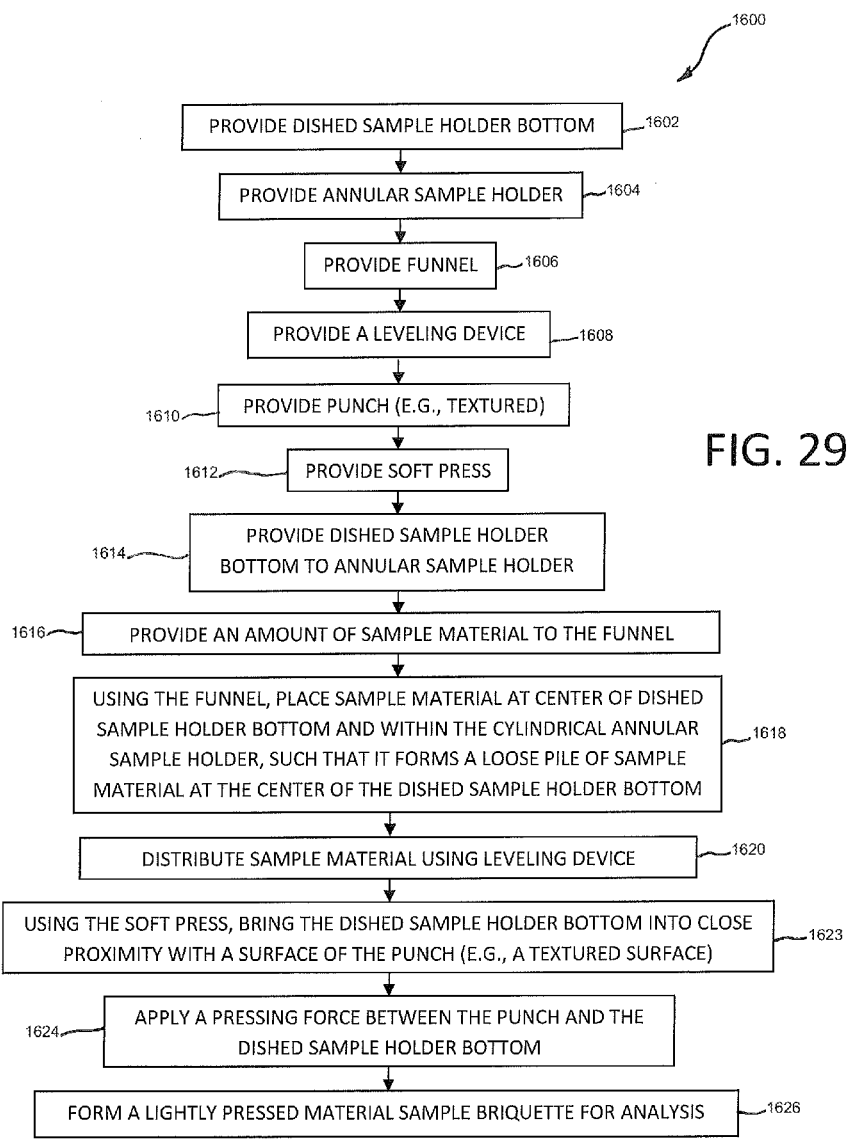
FIG. 29 depicts a method of performing XRD sample preparation according to some embodiments.

FIG. 29 depicts a method 1600 of performing XRD sample preparation according to some embodiments. The method 1600 includes the steps of providing 1602 a dished sample holder bottom, providing 1604 an annular sample holder, providing 1606 a dosing funnel 1304, providing 1608 a leveling device 1000 or apparatus 1400, providing 1610 a punch 1100 such as a textured punch, providing 1612 a soft press, providing 1614 a dished sample holder bottom 500 to an annular sample holder 400, using 1616 the dosing funnel 1304 to dose material 900 to a central portion of the dished sample holder bottom 500, using 1618 the dosing funnel 1304 to provide a predetermined amount of sample material 900 at the center of the dished sample holder bottom 500 and form a loose pile of sample material 900 at the center of the sample holder assembly 600/holder 400, randomly distributing 1622 sample material 900 using a leveling device 1000, bringing 1623 the dished sample holder bottom 500 into close proximity with the textured or flat punch 1100, applying a pressing force 1624 between the textured of flat punch 1100 and the dished sample holder bottom 500, and forming 1626 a lightly-pressed sample pellet having an upper measuring surface suitable for analysis (e.g., for XRD analysis).

Figure 30:
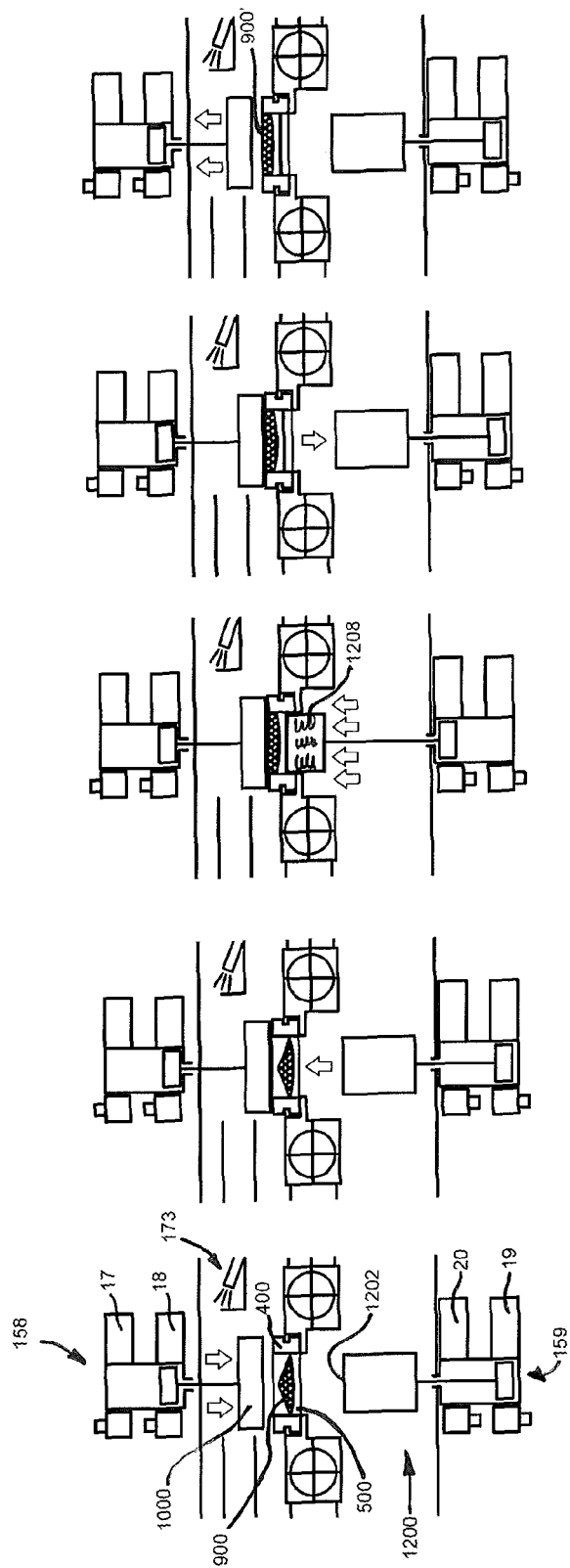
FIG. 30 depicts a sequence of lightly pressing an XRD sample according to some embodiments.

FIG. 30 schematically depicts a sequence of lightly pressing an XRD sample according to some embodiments. The non-limiting example shows a pressed sample pellet 900' which is crack-resistant, being formed in-situ. The pressed sample pellet 900' is formed by providing sample material 900 to the center of a sample holder assembly 600 (e.g., using a chute 820 apparatus, dosing device 1300, spoon 1302, or the like). The sample material 900 is pressed in the annular sample holder 400 by movement of the dished sample holder bottom 500 and movement of the dished sample holder bottom 500 against a textured or flat punch 1100. This is done to create a measuring surface on the upper/top side of the sample material 900 and pressed sample pellet 900' (which comes into contact with the textured or flat punch 1100). Pressure is not applied directly to the measuring surface of the pressed sample pellet 900'; rather, pressure is evenly distributed to the dished sample holder bottom which is moveable with respect to the annular sample holder 400 to avoid over-pressing. If too much pressure is experienced by the dished sample holder bottom 500 and its concave surface 501 is no longer able to distribute the forces, frictional forces between the lip 512 and the inner surface 401 are overcome and the dished sample holder bottom 500 moves to stabilize pressure and avoid build-ups of pressure which would over-press sample material 900. During formation of the pressed sample pellet 900', portions of the sample material 900 which eventually make up the upper measuring surface of the pressed sample pellet 900' only see gentle, indirect forces from the punch 1100 since the concave dished surface 501 and breakaway bottom 500 work in conjunction with each other. Once the material sample pellet 900' is formed, the platform 1206 holding the sample 900' and holder 600 moves along a track 1220 to robot pincers 855, which grab the sample holder assembly 600 by the retaining groove 403 on the outer portion of annular sample holder 400. The sample 900' is placed on a finished sample conveyor 700 for further use and indexed by a stopper 171.

Figure 31A:
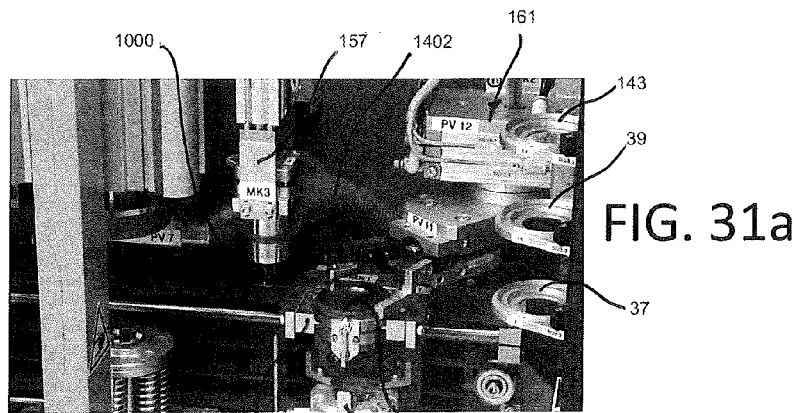
FIGS. 31a-31l show sequence photographs of an XRD sample preparation device in action, according to some embodiments.
Figure 31B:
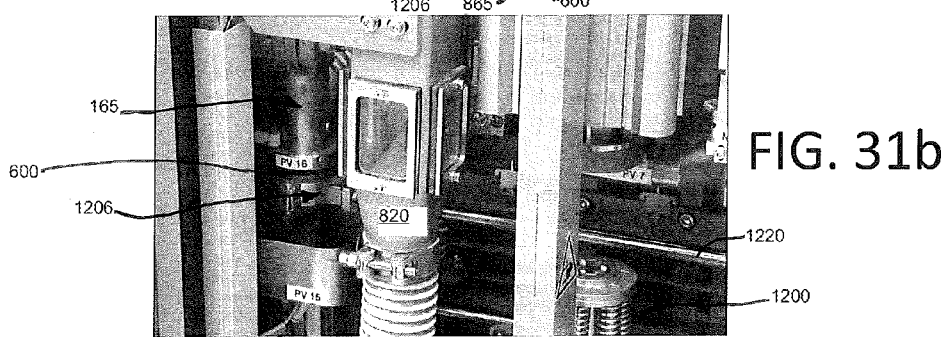
Figure 31C:
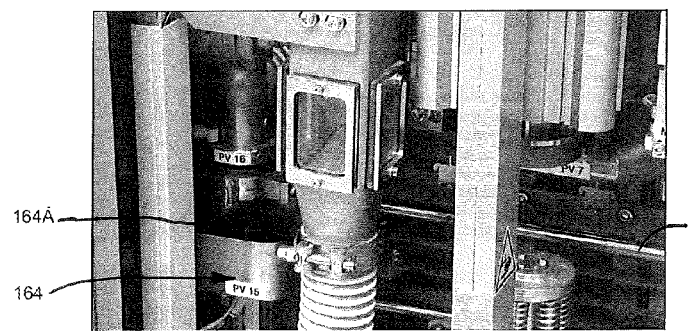
Figure 31D:
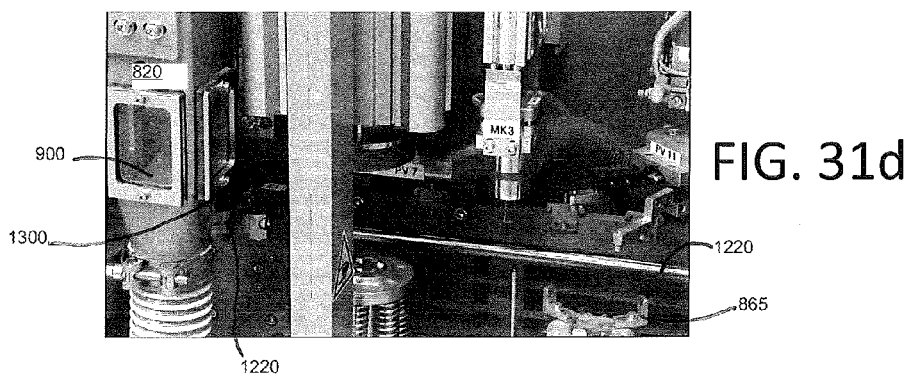
Figure 31E:
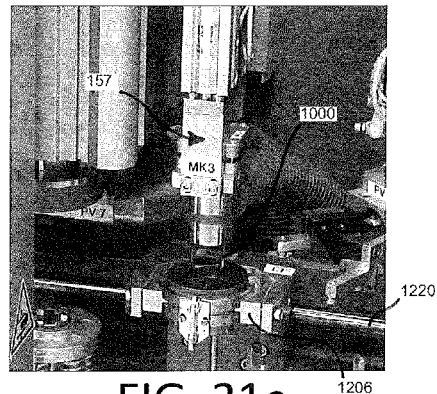
Figure 31F:
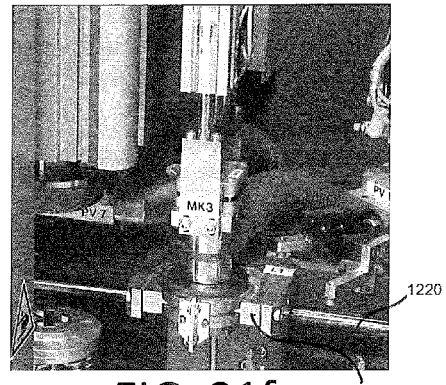
Figure 31G:
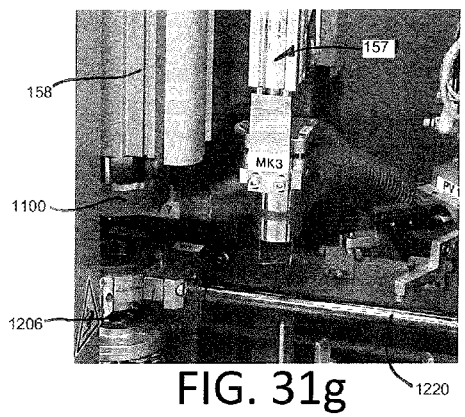
Figure 31H:
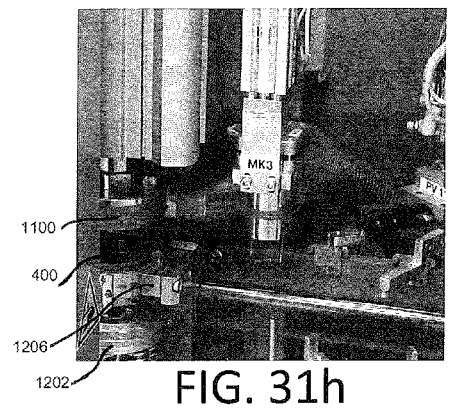
Figure 31I:
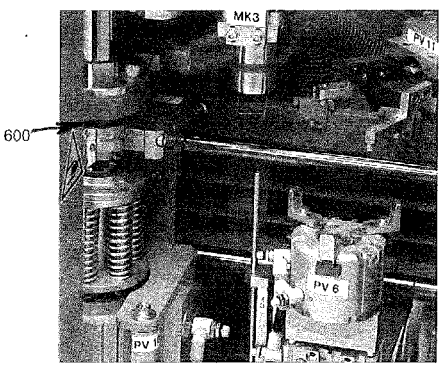
Figure 31J:
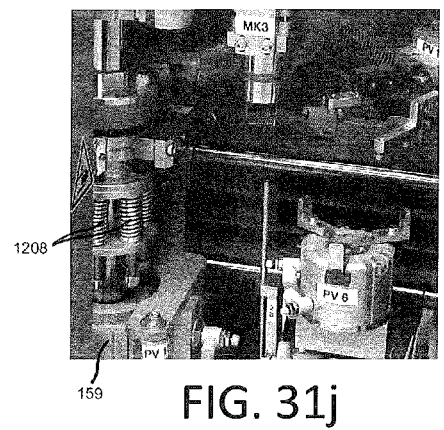
Figure 31K:
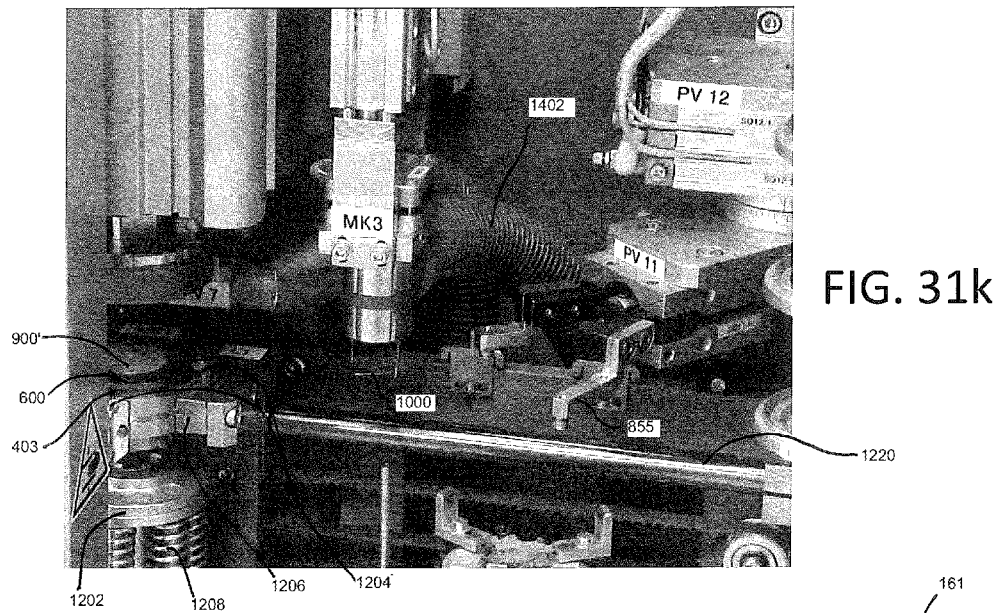
Figure 31L:
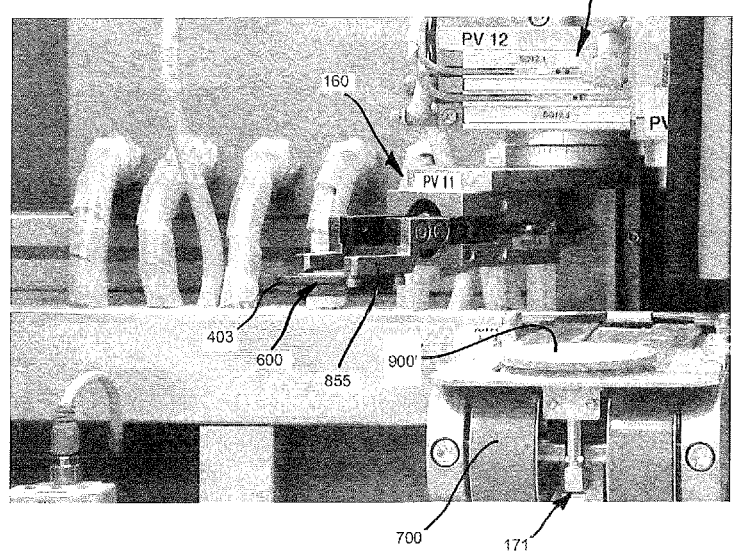

FIGS. 31*a*-31*l* show sequence photographs of an XRD sample preparation device in action, according to some embodiments. FIG. 31*a* shows a photograph of a step of an empty sample holder assembly 600 being delivered to a movable platform 1206 by robot pincers 855. The pincers 855 are controlled by valves 161 and 160 shown in the circuit of FIG. 1. FIG. 31*b* shows a step where the movable platform 1206 transports the empty sample holder assembly 600 to a cleaning station where a hood covers the assembly 600. Inside portions of the empty sample holder assembly 600 may be scrubbed, brushed, and/or air blown using one or more devices 163, 164, and the debris created may be sent to a de-dusting outlet 1401. An actuator 164A may extend upwardly towards the platform 1206 and engage one or more lower portions of the annular sample holder 400 or the dished sample holder bottom 500 as shown in FIG. 31*c*. FIG. 31*d* shows a photograph of the platform 1206 holding the cleaned empty sample holder assembly 600 which has moved along track 1220 so as to position the center of the dished sample holder bottom 500 underneath a dosing funnel 1304. A valve 156 moves a spoon 1302 into chute 820 to receive an amount of sample material 900 disposed within the chute 820, and then into alignment with a dosing funnel 1304 to allow sample material 900 obtained by the spoon 1302 to enter the sample holder assembly 600 in a special manner. FIG. 31*e* shows a leveling device 1000 according to one embodiment being lowered into a sample holder assembly 600 which has been dosed with sample material 900 at its center. FIG. 31*f* shows a machine configuration where the leveling device 1000 (not visible) is in use and in rotation. FIG. 31*g* shows a machine configuration where the leveling device 1000 has been turned off and raised to allow platform 1206 and sample holder assembly 600 to move along a track 1220 and into position over a press 1200 and under a punch 1100 (e.g., a flat or textured punch). FIG. 31*h* shows a configuration where a device 158 lowers the punch 1100 to come into close proximity with the dosed sample holder assembly 600 where it is then held stationary. FIG. 31*i* shows a machine configuration wherein the punch 1100 has been lowered to the annular sample holder 400, and the press 1200 underneath the dished sample holder bottom 400 has been activated. FIG. 31*j* shows a platen 1202 being raised to engage the lower surface 504 of the dished sample holder bottom 500 and press the dished sample holder bottom 500 upwards toward the punch 1100 in order to lightly press the pre-dosed sample material 900 located within the sample holder assembly 600. As shown, a number of springs 1208 may take up slack and uneven loading, and therefore ensure that even pressures are distributed to the sample holder bottom 500 relative to the annular sample holder 400. FIG. 31*k* shows the punch 1100 lifted after pressing, and further shows the exposed upper measuring surface of the lightly pressed briquette sample 900'. The platform 1206 holding the sample 900' is subsequently moved along track 1220 to a location where robot pincers 855 are able to grab the retaining groove 403 of the annular sample holder 400. Device 160 may be configured to close and open the robot pincers 855. The final assembly 600 containing sample 900', holder 400, and bottom 500 may be raised (e.g., via 161) and positioned onto a motor-controlled intermittently-driven finished sample conveyor 700. Individual pressed samples 900' loaded onto the finished sample conveyor 700 may be separated from each other, or otherwise prevented from falling off the conveyor 700 via one or more cartridge conveyor stopper devices 171. Stopper 171 may be of particular benefit when the apparatus 6B is used in an advanced robot lab.

The dished sample holder bottom 500 and its concave surface 501 serves to distribute finely ground sample material 900. Sample material dosing is made automatically to improve sample accuracy, XRD reading precision, and repeatability. The novel "leveling" step using a leveling device 1000 helps center material in a loose format for even compaction during pressing. This helps to randomize crystal orientation and reduce the unwanted effects of preferred orientation. Accordingly, best XRD results may be expected. Lastly, a soft pressing step using punch 1100 may be performed, wherein the punch can be selected from one or more punches. Punch 1100 may comprise a textured surface tool such as a sanded punch or a punch having a textured surface pattern (e.g., a "waffle" pattern), without limitation. This helps to maintain a rough, randomized measuring surface on an upper measuring surface part of the pressed sample 900'.

In some embodiments, different pressures or pressures as a function of time p(t) may be applied during sample preparation. Accordingly, the effects of preferred orientation of certain minerals that might have plate-like or stick-like crystal geometries after grinding (e.g., muscovite and/or calcite) may be more closely controlled. Moreover, in some embodiments, preferred orientation may be further avoided by using very small applied pressures The conventional methods of creating dust samples on greased plates or transmission sample holders (samples placed between two x-ray support films), are both impracticle for automated laboratory environments—and are particularly not suitable for minerals study, because such small dustings are generally not very representative of large quantities of bulk ore having viens of varying mineral deposits. It has been observed that lower pressing pressures yield closer observed intensities ratios with regards to the transmission measurements. Transmission experiments using the apparatus and methods disclosed herein demonstrate an almost perfect statistical distribution of the crystals within a material sample. Measurements with intensities matching the 'ideal' intensity ratio distributions are the best precondition for an accurate analysis. Non-'ideal' intensity ratios may lead to a misinterpretation of the instrumental data—especially in the case of quantitative phase analysis. The best achievable results, excluding transmission experiments, can be obtained by applying low pressure using the novel front-loading sample preparation equipment with smooth pressure regulation.

Rather than the multiple fingers 1010 shown, it is also envisaged that the leveling device may alternatively comprise a single bent wire in any configuration (e.g., such as a "W"-shape "D"-shape, "O"-shape, "T"-shape, "H"-shape, or other shape that would compliment a surface profile of a conical stacked pile of powdered sample material), without limitation.

A contractor or other entity may provide an XRD sample preparation apparatus or operate an XRD sample preparation apparatus in whole, or in part, as shown and described. For instance, the contractor may receive a bid request for a project related to designing or operating an XRD sample preparation apparatus, or the contractor may offer to design any number of XRD sample preparation apparatuses or components thereof, or a process for a client involving one or more of the features shown and described herein. The contractor may then provide, for example, any one or more of the devices or features thereof shown and/or described in the embodiments discussed above. The contractor may provide such devices by selling those devices or by offering to sell those devices. The contractor may provide various embodiments that are sized, shaped, and/or otherwise configured to meet the design criteria of a particular client or customer. The contractor may subcontract the fabrication, delivery, sale, or installation of a component of the devices disclosed, or of other devices used to provide said devices. The contractor may also survey a site and design or designate one or more storage areas for storing the material used to manufacture the devices, or for storing the devices and/or components thereof. The contractor may also maintain, modify, or upgrade the provided devices. The contractor may provide such maintenance or modifications by subcontracting such services or by directly providing those services or components needed for said maintenance or modifications, and in some cases, the contractor may modify a preexisting XRD sample preparation apparatus, subassemblies thereof, components thereof, and/or parts thereof with one or more "retrofit kits" to arrive at a modified apparatus or method of operating an apparatus comprising one or more method steps, devices, components, or features of the systems and processes discussed herein.

Although the invention has been described in terms of particular embodiments and applications, one of ordinary skill in the art, in light of this teaching, can generate additional embodiments and modifications without departing from the spirit of or exceeding the scope of the claimed. For example, in some embodiments, applications of the XRD sample preparation apparatus 6B and methods 1600 shown and described herein may also have usefulness and/or utility in NIR and ED XRF analyses in various industries. Moreover, numerous pressing recipes having multiple defined press conditions may be employed. For example, in some non-limiting embodiments of the invention such as the one shown in FIG. 28, up to 12 or more pressing recipes may be available and may have 4 or more defined press conditions. Capacities may vary from one or two samples every hour, to hundreds of samples per hour. In certain preferred embodiments, such as the one shown in FIG. 8, an XRD sample preparation apparatus may be configured to produce and process no less than 15 samples in an hour.

Accordingly, it is to be understood that the drawings and descriptions herein are proffered by way of example to facilitate comprehension of the invention and should not be construed to limit the scope thereof.

REFERENCE NUMERAL IDENTIFIERS

1 DIGITAL INPUT—INPUT CUP PINCERS—CUP CLOSED (INITIAL POSITION)
2 DIGITAL INPUT—INPUT CUP PINCERS—CUP RELEASED
6A CIRCUIT—XRD SYSTEM
6B PROTOTYPE—XRD SYSTEM
5 DIGITAL INPUT—DOSER BEATER—INITIAL POSITION
7 DIGITAL INPUT—BYPASS DOSER—POSITION ABOVE CARTRIDGE (INITIAL POSITION)
8 DIGITAL INPUT—BYPASS DOSER—POSITION IN BYPASS
9 DIGITAL INPUT—CARTRIDGE PINCERS LIFT—POSITION DOWN (INITIAL POSITION)
10 DIGITAL INPUT—CARTRIDGE PINCERS LIFT—POSITION UP
11 DIGITAL INPUT—CARTRIDGE PINCERS—CARTRIDGE CLOSED (INITIAL POSITION)
12 DIGITAL INPUT—CARTRIDGE PINCERS—CARTRIDGE RELEASED
13 DIGITAL INPUT—CARTRIDGE PRESS CLEANER—POSITION PUSHED IN (INITIAL POSITION)
14 DIGITAL INPUT—CARTRIDGE PRESS CLEANER—PUSHED OUT
15 DIGITAL INPUT—SAMPLE PREPARATION LIFT—POSITION UP (INITIAL POSITION)
16 DIGITAL INPUT—SAMPLE PREPARATION LIFT—POSITION DOWN
17 DIGITAL INPUT—UPPER CARTRIDGE PRESS—POSITION UP (INITIAL POSITION)
18 DIGITAL INPUT—UPPER CARTRIDGE PRESS—POSITION DOWN
19 DIGITAL INPUT—LOWER CARTRIDGE PRESS—POSITION DOWN (INITIAL POSITION)
20 DIGITAL INPUT—LOWER CARTRIDGE PRESS—POSITION UP
21 DIGITAL INPUT—OUTPUT SAMPLE PINCERS—SAMPLE CLOSED (INITIAL POSITION)
22 DIGITAL INPUT—OUTPUT SAMPLE PINCERS—SAMPLE RELEASED
23 DIGITAL INPUT—OUTPUT SAMPLE PINCERS MOVING—POSITION CARTRIDGE PREPARATION (INITIAL POSISTION)
24 DIGITAL INPUT—OUTPUT SAMPLE PINCERS MOVING—INTO POSITION OUTPUT
25 DIGITAL INPUT—INPUT CUP PINCERS MOVING—POSITION FOR ROBOT INPUT (INITIAL POSITION)
26 DIGITAL INPUT—INPUT CUP PINCERS MOVING—POSITION FOR HAND SAMPLE INPUT
27 DIGITAL INPUT—CARTRIDGE PREPARATION CYLINDER—POSITION UP (INITIAL POSITION)
28 DIGITAL INPUT—CARTRIDGE PREPARATION CYLINDER—POSITION DOWN
29 DIGITAL INPUT—SAMPLE EJECTOR—POSITION DOWN (INITIAL POSITION)
30 DIGITAL INPUT—SAMPLE EJECTOR—POSITION UP
34 DIGITAL INPUT—CUP ON ROBOT CUP CONVEYOR IN ROBOT POSITION—PRESENT
35 DIGITAL INPUT—CUP ON ROBOT CUP CONVEYOR IN PINCERS POSITION—PRESENT
37 DIGITAL INPUT—CUP ON CARTRIDGE CONVEYOR IN PINCERS POSITION—PRESENT
39 DIGITAL INPUT—CUP ON HAND SAMPLE CUP CONVEYOR IN PINCERS POSITION—PRESENT
40 DIGITAL INPUT—CARTRIDGE IN HOLDER NO. 1—PRESENT
143 STEPPER CONTROLLER—CARTRIDGE MOVING STEPPING MOTOR—LIMIT POSITION SAMPLE TAKING
144 STEPPER CONTROLLER—CARTRIDGE MOVING STEPPING MOTOR—LIMIT POSITION CLEANING
149 OPTION—HAND SAMPLE
150 VALVE—INPUT CUP PINCERS—CUP CLOSE/RELEASE
151 VALVE—INPUT CUP DISCHARGING—DISCHARGE/NOT DISCHARGE
152 VALVE—DOSER BEATER—ON
153 VALVE—BYPASS DOSER—INTO POSITION BYPASS
154 VALVE—CARTRIDGE PINCERS LIFT—INTO POSITION UP/DOWN
155 VALVE—CARTRIDGE PINCERS—CARTRIDGE CLOSE/OPEN
156 VALVE—CARTRIDGE PRESS CLEANER—PUSH OUT
157 VALVE—SAMPLE PREPARATION LIFT—INTO POSITION DOWN
158 VALVE—UPPER CARTRIDGE PRESS—INTO POSITION DOWN
159 VALVE—LOWER CARTRIDGE PRESS—INTO POSITION UP/DOWN
160 VALVE—OUTPUT SAMPLE PINCERS—SAMPLE CLOSE/OPEN
161 VALVE—OUTPUT SAMPLE PINCERS MOVING—INTO POSITION CARTRIDGE PREPARATION/OUTPUT
162 VALVE—INPUT CUP PINCERS MOVING—INTO POSITION FOR ROBOT INPUT/HAND SAMPLE INPUT
163 VALVE—CARTRIDGE PREPARATION CYLINDER—INTO POSITION DOWN
164 VALVE—SAMPLE EJECTOR—INTO POSITION UP
164A ACTUATOR
165 VALVE—CARTRIDGE CLEANING JET AIR—ON
166 VALVE—CLEANING DEDUSTING VALVE—OPEN
167 VALVE—DOSING DEDUSTING VALVE—OPEN
168 VALVE—PRESS DEDUSTING VALVE—OPEN
169 VALVE—PREPARATION DEDUSTING VALVE—OPEN
170 VALVE—CARTRIDGE LIFT STOPPER INTO POSITION UP (INITIAL POSITION)/DOWN
171 VALVE—CARTRIDGE CONVEYOR STOPPER IN TO POSITION UP (INITIAL POSITION)/DOWN
172 VALVE—SAMPLE PREPARATION JET AIR—ON
173 VALVE—CARTRIDGE PRESS CLEANER JET AIR—ON
180 OPTION
181 OPTION
182 OPTION
183 MOTOR
184 MOTOR
185 MOTOR
186 CUP OF SAMPLE MATERIAL
300 PRESSED MATERIAL SAMPLE—THIN LAYER
301 PLATE

302 CRYSTALS WITH PREFERRED ORIENTATION
303 SURFACE
310 DUSTED MATERIAL SAMPLE—THIN LAYER
311 PLATE
312 CRYSTALS WITH RANDOM ORIENTATION
313 GREASED SURFACE
400 ANNULAR SAMPLE HOLDER
401 INNER SURFACE
402 OUTER SURFACE
403 RETAINING GROOVE
404 LOWER SURFACE
405 UPPER SURFACE
406 GROOVE SURFACES
500 DISHED SAMPLE HOLDER BOTTOM
501 DISHED SURFACE (I.E., CONCAVE)
502 LOWER SURFACE
503 GROOVE
504 CLEARANCE
505 OUTER SURFACE
510 SEAL RING
511 RECESS
512 OUTER LIP
513 INNER PORTION
600 SAMPLE HOLDER ASSEMBLY
700 FINISHED SAMPLE CONVEYOR
810 HAND SAMPLING CUP CONVEYOR
820 CHUTE
830 ROBOT CUP CONVEYOR
840 ROBOT ARM
842 JOINT
845 ROBOT PINCERS
855 ROBOT PINCERS
865 ROBOT PINCERS
900 SAMPLE MATERIAL
900' LIGHTLY PRESSED SAMPLE PELLET FOR XRD ANALYSIS
1000 LEVELING DEVICE
1001 PROXIMAL MOUNT
1002 TAPER
1003 SHAFT
1004 TOP END
1005 UPPER SECTION
1006 LOWER SECTION
1007 TAPERED SURFACE PORTION
1008 ENLARGED UPPER PORTION
1009 OPENING
1010 FINGER
1011 LONGEST FINGER
1012 FIRST FINGER
1013 SECOND FINGER
1014 THIRD FINGER
1015 FOURTH FINGER
1016 SHORTEST FINGER
1020 TIP
1030 FINGER DISTAL END
1100 TEXTURED OR FLAT PUNCH
1101 BOSS (OPTIONAL)
1102 TEXTURED/SANDED SURFACE
1103 UPPER SURFACE
1104 LOWER SURFACE
1200 PRESS
1202 PLATEN
1204 RETAINING CLAW
1206 CARTRIDGE/PLATFORM
1208 SPRINGS
1220 TRACK
1300 DOSING DEVICE
1301 EXHAUSTING PORT
1302 SPOON/OPENING
1303 PISTON ROD
1304 DOSING FUNNEL
1305 PLUNGER
1306 SPRING
1307 PLUNGING SURFACE
1400 LEVELING/CLEANING DEVICE
1401 DEDUSTING OUTLET
1402 DEDUSTING OUTLET
1501 CONVENTIONAL PHI ROTATION RESULTS ACHIEVED BY HAND FOR FIRST QUARTZ SAMPLE
1502 CONVENTIONAL PHI ROTATION RESULTS ACHIEVED BY HAND FOR SECOND QUARTZ SAMPLE
1503 CONVENTIONAL PHI ROTATION RESULTS ACHIEVED BY HAND FOR MUSCOVITE (MICA) SAMPLE
1504 CONVENTIONAL PHI ROTATION RESULTS ACHIEVED BY HAND FOR ORTHOCLASE SAMPLE
1511 PHI ROTATION RESULTS ACHIEVED FOR FIRST QUARTZ SAMPLE
1512 PHI ROTATION RESULTS ACHIEVED FOR SECOND QUARTZ SAMPLE
1513 PHI ROTATION RESULTS ACHIEVED FOR MUSCOVITE (MICA) SAMPLE
1514 PHI ROTATION RESULTS ACHIEVED FOR ORTHOCLASE (FELDSPAR) SAMPLE
1600 METHOD
1602-1626 STEPS

What is claimed is:

1. A sample preparation apparatus configured to prepare a material sample suitable for X-ray diffraction comprising:
a dished sample holder bottom configured to fit within an annular sample holder, the dished sample holder bottom having a concave dished surface which is configured to distribute sample material under pressing forces;
wherein the dished sample holder is provided within the annular sample holder and is configured to move within the annular sample holder in piston fashion;
wherein said dished sample holder bottom further comprises a seal ring disposed between the inner surface of the annular sample holder and an outer surface of the dished sampled holder bottom.

2. The sample preparation apparatus according to claim 1, wherein said seal ring is disposed in a retaining groove provided on the outer surface comprised of a number of groove surfaces.

3. The sample preparation apparatus according to claim 1, wherein said seal ring comprises an outer lip and an inner portion.

4. The sample preparation apparatus according to claim 3, wherein said seal ring further comprises a recess between said outer lip and inner portion.

5. The sample preparation apparatus according to claim 1, wherein the annular sample holder further comprises a retaining groove provided at its outer surface which is configured to receive one or more retaining claws.

6. The sample preparation apparatus according to claim 1, wherein the dished sample holder bottom is used in a front-loading process, and wherein the sample preparation apparatus is configured to produce a quality material sample suitable for X-ray diffraction via said front-loading process.

7. A method of preparing a material sample suitable for X-ray diffraction comprising:

dosing a dished sample holder bottom configured to fit within an annular sample holder with sample material, the dished sample holder bottom having a concave dished surface which is configured to distribute sample material under pressing forces;

pressing the sample material; and distributing sample material within the dished sample holder bottom by virtue of the concave dished surface;

wherein the step of dosing comprises bringing a leveling device into contact with said sample material prior to pressing, the leveling device comprising a shaft, and a plurality of fingers having different lengths.

8. The method of claim 7, wherein the step of dosing further comprises a dosing funnel configured to place the sample material in central portions of the dished sample holder bottom.

9. The method of claim 7, wherein the step of pressing further comprises avoiding over-pressing of the sample material.

10. The method of claim 7, wherein the step of pressing further comprises pressing with a textured or flat punch.

11. The method of claim 7, wherein all steps are automated and part of a front-loading process.

12. The method of claim 7, wherein distal ends of the fingers are further from a tip at a radially outwardly portion of the leveling device, and closer to a tip at a radially inwardly portion of the leveling device.

* * * * *